(12) United States Patent
Storz

(10) Patent No.: US 11,466,014 B2
(45) Date of Patent: Oct. 11, 2022

(54) PROCESS FOR PREPARING SOLUBLE GUANYLATE CYCLASE STIMULATORS

(71) Applicant: Cyclerion Therapeutics, Inc., Cambridge, MA (US)

(72) Inventor: Thomas Storz, Lowell, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 10 days.

(21) Appl. No.: 16/976,249

(22) PCT Filed: Mar. 7, 2019

(86) PCT No.: PCT/US2019/021076
§ 371 (c)(1),
(2) Date: Aug. 27, 2020

(87) PCT Pub. No.: WO2019/173548
PCT Pub. Date: Sep. 12, 2019

(65) Prior Publication Data
US 2021/0032254 A1 Feb. 4, 2021

Related U.S. Application Data

(60) Provisional application No. 62/639,642, filed on Mar. 7, 2018.

(51) Int. Cl.
*C07D 487/04* (2006.01)

(52) U.S. Cl.
CPC .................. *C07D 487/04* (2013.01)

(58) Field of Classification Search
CPC .................................................. C07D 487/04
USPC ........................................................ 544/349
See application file for complete search history.

(56) References Cited

U.S. PATENT DOCUMENTS

2018/0065971 A1* 3/2018 Rennie ............... A61K 31/4985

FOREIGN PATENT DOCUMENTS

WO    2016044446 A2    3/2016
WO    2018045276 A1    3/2018

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Wu et al., Synthesis and photoelectric properties of a solution-processable yellow-emitting iridium(iii) complex. New Journal of Chemistry, 2015;39:8909-8914.
International Search Report and Written Opinion for Application No. PCT/US2019/021076, dated May 8, 2019, 10 pages.

* cited by examiner

*Primary Examiner* — Douglas M Willis
(74) *Attorney, Agent, or Firm* — McCarter & English, LLP; Xin Zhang; James M. Alburger

(57) ABSTRACT

The invention relates to novel methods for preparing 3-substituted 1,2,4-triazole compounds of Formula IA:

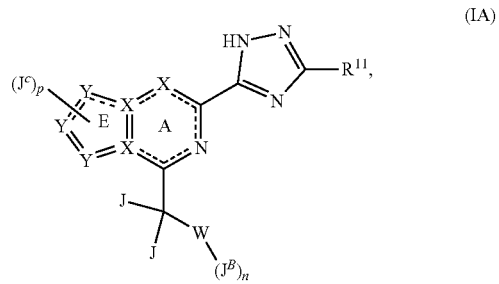

as sGC stimulators. The method comprises reacting the amidrazone compound represented by Formula IIA:

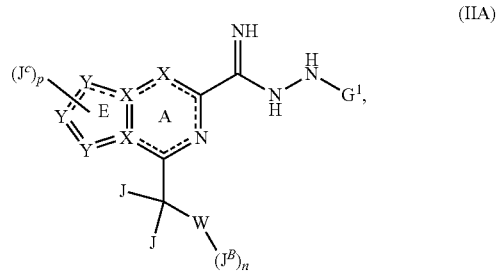

or a salt thereof, with a carboxylic acid, an activated ester, a thioester, an acid halide, a thioacyl halide, or an acid anhydride in the presence of a base.

11 Claims, No Drawings

PROCESS FOR PREPARING SOLUBLE GUANYLATE CYCLASE STIMULATORS

RELATED APPLICATIONS

This application is a 35 U.S.C. § 371 national stage filing of International Application No. PCT/US2019/021076, filed on Mar. 7, 2019, which in turn claims the benefit of the filing date, under 35 U.S.C. § 119(e), of U.S. Provisional Application No. 62/639,642, filed on Mar. 7, 2018. The entire contents of each of the foregoing applications are incorporated herein by reference.

FIELD OF THE INVENTION

The present invention relates to novel methods for preparing soluble guanylate cyclase (sGC) stimulators.

BACKGROUND OF THE INVENTION

Compounds that stimulate soluble guanylate cyclase (sGC) can be used to treat many diseases and conditions in which an increase in the concentration of nitric oxide (NO) or cyclic guanosine 3',5'-monophosphate (cGMP) or both, or wherein an upregulation of the NO pathway is desirable. Such diseases and conditions include, but not limited to pulmonary hypertension, arterial hypertension, heart failure, atherosclerosis, inflammation, thrombosis, renal fibrosis and failure, liver cirrhosis, erectile dysfunction, female sexual disorders, disorders related to diabetes, ocular disorders and other related cardiovascular disorders. sGC stimulators offer considerable advantages over other current alternative therapies that either target the aberrant NO pathway or that are directed at diseases wherein upregulation of the NO pathway is beneficial.

sGC stimulators are disclosed in U.S. application Ser. No. 15/693,758, the entire teachings of which are incorporated herein by reference. Successful commercialization of a new therapeutic agent requires an efficient process for preparing the agent in high yield and purity. Therefore, there still exists a need for improved processes for preparing the sGC stimulators that are more efficient and suitable for large scale manufacturing process.

SUMMARY OF THE INVENTION

The present invention provides various methods for preparing 3-substituted 1,2,4-triazole compounds as sGC stimulators and their synthetic precursors. Compared to the previously disclosed method, the processes of the present invention can produce the sGC stimulators with higher yield and high purity. Specifically, the present methods can produce the sGC stimulators via a shortened, more practical and higher-yielding synthetic sequence that delivers the final product in much higher purity while eliminating all chromatographic purifications and use of hazardous hydrazine as reagent (hence more suitable for large scale manufacturing). These processes are more suitable for large scale manufacturing process.

In a first aspect, disclosed herein is a process for preparing a 3-substituted 1,2,4-triazole compound, comprising reacting an amidrazone compound with a carboxylic acid, an activated ester, a thioester, an acid halide, a thioacyl halide or an acid anhydride in the presence of a base. When the carboxylic acid is used, an activating agent is also present. The amidrazone compound comprises an amidrazone bonded to an optionally substituted aryl or heteroaryl; the substituent at the 3 position of the 3-substituted 1,2,4-triazole compound is the optionally substituted aryl or heteroaryl bonded to the amidrazone compound; and the 3-substituted 1,2,4-triazole compound may be optionally substituted at the 5-position.

The disclosed process can be advantageously used to prepare the 3-substituted 1,2,4-triazole compounds disclosed in U.S. application Ser. No. 15/693,758. Specifically, a first embodiment of the first aspect is a process of preparing a 3-substituted 1,2,4-triazole compound represented by Formula IA:

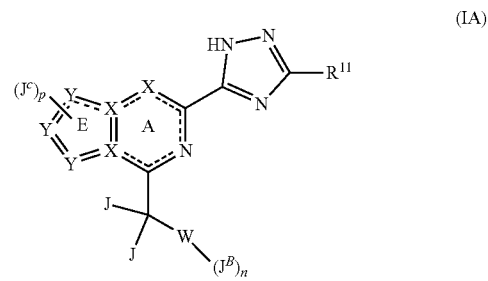

(IA)

or a salt thereof. The process comprises reacting the amidrazone compound represented by Formula IIA:

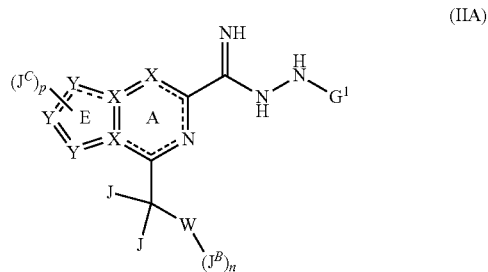

(IIA)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. The values of the variables in Formula IA, Formula IIA, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are defined as follows:

rings E and A form the core of the molecule and are aromatic; each instance of X and Y is independently selected from N, $NR''$ and C; wherein a maximum of 4 instances of X and Y are simultaneously N and $R''$ is H or $C_{1-6}$alkyl;

W is either i) absent, with $J^B$ connected directly to the carbon atom bearing two J groups, each J is independently hydrogen or methyl, n is 1 and $J^B$ is a $C_{1-7}$ alkyl chain optionally substituted by up to 9 instances of fluorine; or ii) a ring B that is a phenyl, a $C_{3-7}$ cycloalkyl ring or a 5 or 6-membered heteroaryl ring, containing 1 or 2 ring nitrogen atoms;

wherein when ring B is the phenyl or 5 or 6-membered heteroaryl ring; each J is independently hydrogen or methyl; n is an integer selected from 0 to 3; and each $J^B$ is independently selected from halo, —CN, a $C_{1-6}$ aliphatic, —$OR^B$ and a $C_{3-8}$ cycloaliphatic ring; and wherein when ring B is the $C_{3-7}$ cycloalkyl ring; each J is hydrogen; n is an integer selected from 0 to 3 and each $J^B$ is independently selected from halo, —CN, a $C_{1-6}$ aliphatic and —$OR^{B1}$;

wherein each $J^B$ that is a $C_{1-6}$ aliphatic and each $J^B$ that is a $C_{3-8}$ cycloaliphatic ring are optionally and independently substituted with up to 3 instances of $R^3$;

each $R^B$ is independently a $C_{1-6}$ aliphatic or a $C_{3-8}$ cycloaliphatic ring; said $R^B$ is optionally and independently substituted with up to 3 instances of Ria;

each $R^{B1}$ is independently selected from hydrogen, a $C_{1-6}$ aliphatic and a $C_{3-8}$ cycloaliphatic ring; wherein each of said $C_{1-6}$ aliphatic and each of said $C_{3-8}$ cycloaliphatic ring are optionally and independently substituted with up to 3 instances of $R^{3b}$;

each $R^3$, $R^{3a}$ and $R^{3b}$ is, in each instance, independently selected from halo, —CN, $C_{1-4}$ alkyl, $C_{1-4}$ haloalkyl, —O($C_{1-4}$ alkyl) and —O($C_{1-4}$ haloalkyl);

p is an integer selected from 1, 2 and 3;

each $J^C$ is independently selected from hydrogen, halo, $C_{1-4}$ aliphatic, $C_{1-4}$ alkoxy and —CN; wherein each said $C_{1-4}$ aliphatic and $C_{1-4}$ alkoxy is optionally and independently substituted by up to 3 instances of $C_{1-4}$ alkoxy, $C_{1-4}$haloalkoxy, —OH or halo;

$R^{11}$ is H, —$NR^{a2}R^{b2}$, —$C(O)NR^{a2}R^{b2}$, —$C(O)R^{15a}$, —CN, $C_{2-6}$ alkenyl optionally and independently substituted with 0-2 occurrences of $R^{b2}$, $C_{2-6}$ alkynyl optionally and independently substituted with 0-2 occurrences of $R^{b2}$; $C_{1-6}$ alkyl optionally and independently substituted with 0-3 occurrences of $R^{15}$, $C_{1-6}$ alkoxy optionally and independently substituted with 0-5 occurrences of $R^{15}$, phenyl optionally and independently substituted with 0-3 occurrences of $R^{15}$, 5- to 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$; wherein each of said 5- to 6-membered heteroaryl and each of said 3-8 membered heterocyclyl contain up to 3 ring heteroatoms independently selected from N, O and S;

$R^{15}$ is halo, —$OR^{b2}$, —$SR^{b2}$, —$NR^{a2}R^{b2}$, —$C(O)R^{b2}$, —$C(O)NR^{a2}R^{b2}$, —$NR^{b2}C(O)OR^{b2}$, —$OC(O)NR^{a2}R^{b2}$, $C_{2-4}$ alkenoxy, $C_{3-8}$ cycloalkyl optionally and independently substituted with 0-3 occurrences of $R^{18}$, phenyl optionally and independently substituted with 0-3 occurrences of $R^{18}$, 5- or 6-membered heteroaryl optionally and independently substituted with 0-3 occurrences of $R^{18}$ or 3-10 membered heterocyclyl optionally and independently substituted with 0-3 occurrences of $R^{18}$; wherein each of said 5- or 6-membered heteroaryl ring and each of said 3-10 membered heterocyclyl contain up to 3 ring heteroatoms independently selected from N, O and S;

$R^{15a}$ is $C_{3-8}$ cycloalkyl optionally and independently substituted with 0-3 occurrences of $R^{18}$, phenyl optionally and independently substituted with 0-3 occurrences of $R^{18}$, 5- or 6-membered heteroaryl optionally and independently substituted with 0-3 occurrences of $R^{18}$ or 3-10 membered heterocyclyl optionally and independently substituted with 0-3 occurrences of $R^{18}$; wherein each of said 5- or 6-membered heteroaryl ring and each of said 3-10 membered heterocyclyl contain up to 3 ring heteroatoms independently selected from N, O and S;

each $R^{18}$ is independently selected from halo, hydroxyl, $C_{1-6}$ alkyl, $C_{1-6}$ alkoxy, $C_{1-6}$ haloalkyl and phenyl;

$R^{a2}$ is hydrogen, —$C(O)R^{b2}$, $C_{1-6}$ alkyl or $C_{1-6}$ haloalkyl;

$R^{b2}$ is hydrogen, $C_{1-6}$ alkyl or $C_{1-6}$ haloalkyl;

X' is a halide;

OE' is a leaving group of an activated ester;

SR' is a leaving group of a thioester;

R" is $C(O)R^{11}$, $C(O)R^{11a}$, $N=CR^{11b}R^{11c}$, $P(O)(OH)_2$, or $PH(O)OH$;

$R^{11a}$ is a $C_{1-6}$alkyl;

$R^{11b}$ and $R^{11c}$ are each independently a $C_{1-6}$ alkyl or phenyl, or $R^{11b}$ and $R^{11c}$ together with the carbon atom from which they are attached form a $C_{4-6}$cycloalkyl; and $G^1$ is an amidrazone protecting group.

In a second aspect, the present invention provides synthetic intermediates for the processes of the present invention. A first embodiment of the second aspect is a compound represented by Formula IIA:

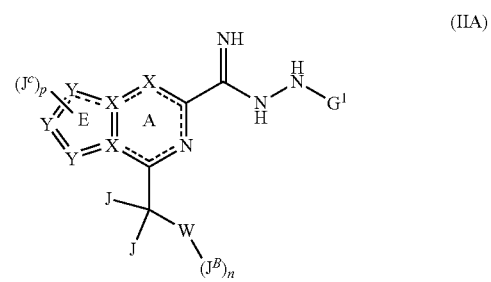

or a salt thereof, wherein:

rings E and A form the core of the molecule and are aromatic; each instance of X and Y is independently selected from N, NR" and C; wherein a maximum of 4 instances of X and Y are simultaneously N and R" is H or $C_{1-6}$alkyl;

W is either i) absent, with $J^B$ connected directly to the carbon atom bearing two J groups, each J is independently hydrogen or methyl, n is 1 and $J^B$ is a $C_{1-7}$ alkyl chain optionally substituted by up to 9 instances of fluorine; or ii) a ring B that is a phenyl, a $C_{3-7}$ cycloalkyl ring or a 5 or 6-membered heteroaryl ring, containing 1 or 2 ring nitrogen atoms;

wherein when ring B is the phenyl or 5 or 6-membered heteroaryl ring; each J is independently hydrogen or methyl; n is an integer selected from 0 to 3; and each $J^B$ is independently selected from halo, —CN, a $C_{1-6}$ aliphatic, —$OR^B$ and a $C_{3-8}$ cycloaliphatic ring; and wherein when ring B is the $C_{3-7}$ cycloalkyl ring; each J is hydrogen; n is an integer selected from 0 to 3 and each $J^B$ is independently selected from halo, —CN, a $C_{1-6}$ aliphatic and —$OR^{B1}$;

wherein each $J^B$ that is a $C_{1-6}$ aliphatic and each $J^B$ that is a $C_{3-8}$ cycloaliphatic ring are optionally and independently substituted with up to 3 instances of $R^3$;

each $R^B$ is independently a $C_{1-6}$ aliphatic or a $C_{3-8}$ cycloaliphatic ring; said $R^B$ optionally and independently substituted with up to 3 instances of $R^{3a}$;

each $R^{B1}$ is independently selected from hydrogen, a $C_{1-6}$ aliphatic and a $C_{3-8}$ cycloaliphatic ring; wherein each of said $C_{1-6}$ aliphatic and each of said $C_{3-8}$ cycloaliphatic ring are optionally and independently substituted with up to 3 instances of $R^{3b}$;

each $R^3$, $R^{3a}$ and $R^{3b}$ is, in each instance, independently selected from halo, —CN, $C_{1-4}$ alkyl, $C_{1-4}$ haloalkyl, —O($C_{1-4}$ alkyl) and —O($C_{1-4}$ haloalkyl);

p is an integer selected from 1, 2 or 3;

each $J^C$ is independently selected from hydrogen, halo, $C_{1-4}$ aliphatic, $C_{1-4}$ alkoxy and —CN; wherein each said $C_{1-4}$ aliphatic and $C_{1-4}$ alkoxy is optionally and independently substituted by up to 3 instances of $C_{1-4}$ alkoxy, $C_{1-4}$ haloalkoxy, —OH or halo; and $G^1$ is an amidrazone protecting group or a salt thereof.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein can be combined with one or more other embodiments of the invention, unless explicitly disclaimed or improper. Combination of embodiments are not limited to those specific combinations claimed via the multiple dependent claims.

Definitions

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

As described herein, compounds of Formula IA or IIA may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. The term "optionally and independently" may be used to describe this situation. As an example, one substituent disclosed herein is $R^{11}$, which may be, among other options, $C_{1-6}$ alkyl optionally and independently substituted with 0-3 occurrences of $R^{15}$. In this instance, the $C_{1-6}$ alkyl may be "optionally substituted": it may be unsubstituted (i.e., 0 occurrences of $R^{15}$) or substituted (i.e., 1, 2, or 3 occurrences of $R^{15}$). When there are multiple occurrences of $R^{15}$ (e.g., 2), each $R^{15}$ may be the same substituent (e.g., two fluoro atoms) or different (e.g., —OH and chloro). As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. A group having from 0-3 atoms could have 0, 1, 2, or 3 atoms. When any variable occurs more than one time at any position, its definition on each occurrence is independent from every other occurrence.

A compound, such as the compounds of Formula IA or IIA or other compounds herein disclosed, may be present in its free form (e.g. an amorphous form, or a crystalline form or a polymorph). Under certain conditions, compounds may also form co-forms. As used herein, the term co-form is synonymous with the term multi-component crystalline form. The formation of a salt is determined by how large the difference is in the pKas between the partners that form the mixture. For purposes of this disclosure, compounds include pharmaceutically acceptable salts, even if the term "pharmaceutically acceptable salts" is not explicitly noted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group" or "aliphatic chain", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 or 1-2 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. An aliphatic group will be represented by the term "$C_{x\text{-}y}$ aliphatic"; wherein x and y are the minimum and the maximum number of carbon atoms forming the aliphatic chain.

The term "alkyl" (as in "alkyl chain" or "alkyl group"), as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-7 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl (sec-butyl), t-butyl, pentyl, hexyl, heptyl, octyl and the like. An alkyl group will be represented by the term "$C_{x\text{-}y}$ alkyl"; wherein x and y are the minimum and the maximum number of carbon atoms forming the alkyl chain.

The term "alkenyl" (as in "alkenyl chain" or "alkenyl group"), refers to a linear or branched-chain monovalent hydrocarbon radical with at least one site of unsaturation, i.e., a carbon-carbon, $sp^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like. An alkenyl group will be represented by the term "$C_{x\text{-}y}$ alkenyl"; wherein x and y are the minimum and the maximum number of carbon atoms forming the alkenyl chain.

The term "alkynyl" (as in "alkynyl chain" or "alkynyl group"), refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like. An alkynyl group will be represented by the term "$C_{x\text{-}y}$ alkynyl"; wherein x and y are the minimum and the maximum number of carbon atoms forming the alkynyl chain.

The term "cycloaliphatic" (or "non-aromatic carbocycle", "non-aromatic carbocyclyl", "non-aromatic carbocyclic" or "cycloaliphatic ring") refers to a cyclic hydrocarbon that is completely saturated or that contains one or more units of unsaturation but which is not aromatic, and which has a single point of attachment to the rest of the molecule. In one embodiment, the term "cycloaliphatic" refers to a monocyclic $C_{3\text{-}8}$ hydrocarbon or a monocyclic $C_{3\text{-}12}$ hydrocarbon. A cycloaliphatic ring will be represented by the term "$C_{x\text{-}y}$ cycloaliphatic"; wherein x and y are the minimum and the maximum number of carbon atoms forming the cycloaliphatic ring. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

"Cycloalkyl" or "cycloalkyl ring", as used herein, refers to a ring system in which is completely saturated and which has a single point of attachment to the rest of the molecule. In one embodiment, the term "cycloalkyl" refers to a monocyclic $C_{3\text{-}12}$ saturated hydrocarbon. For example, the term "cycloalkyl" refers to a monocyclic $C_{3\text{-}7}$ saturated hydrocarbon or a monocyclic $C_{3\text{-}8}$ saturated hydrocarbon. Suitable cycloalkyl groups include, but are not limited to, cyclopropyl, cyclobutyl, cyclopentyl, cyclohexyl, cycloheptyl, norbornyl, cyclooctyl, cyclononyl, cyclodecyl, cycloundecyl, cyclododecyl, and the like. A cycloalkyl ring will be represented by the term "$C_{x\text{-}y}$ cycloalkyl"; wherein x and y are the minimum and the maximum number of carbon atoms forming the cycloalkyl ring.

As used herein, an "aryl" refers to substituted or unsubstituted single-ring aromatic groups in which each atom of the ring is carbon. Preferably the ring is a 5- to 7-membered ring, more preferably a 6-membered ring. Aryl groups include, but are not limited to, phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls, or aromatic rings. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 carbon atoms in the ring, preferably from 5 to 7. For example, aryl groups include, but are not limited to, phenyl (benzene), tolyl, anthracenyl, fluorenyl, indenyl, azulenyl, and naphthyl, as well as benzo-fused carbocyclic moieties such as 5,6,7,8-tetrahydronaphthyl, and the like. In some embodiments, the aryl is a single-ring aromatic group. In some embodiments, the aryl is a two-ring aromatic group. In some embodiments, the aryl is a three-ring aromatic group.

"Heterocycle" (or "heterocyclyl" or "heterocyclic or "heterocyclic ring"), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term could be used in the phrase "aromatic heterocycle", and in this case it would refer to a "heteroaryl group" as defined below. In some embodiments, the heterocycle has 3-8 ring members or 3-10 ring members in which one or more ring members is a heteroatom independently selected from nitrogen, oxygen or sulfur. In other embodiments, a heterocycle may be a monocycle having 3-7 ring members (2-6 carbon atoms and 1-4 heteroatoms). For Example, up to 3 ring heteroatoms independently selected from from nitrogen, oxygen or sulfur.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl.

The term "heteroaryl" (or "heteroaromatic" or "heteroaryl group" or "aromatic heterocycle" or "heteroaryl ring") used alone or as part of a larger moiety as in "heteroarylalkyl" or "heteroarylalkoxy" refers to a ring which is aromatic and contains one or more ring heteroatoms (e.g., one or two ring nitrogen atoms), has between 5 and 6 ring members and which has a single point of attachment to the rest of the molecule. Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl.

The term "ring atom" refers to an atom such as C, N, O or S that is part of the ring of an aromatic ring, a cycloaliphatic ring, a heterocyclic or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, including any oxidized form of nitrogen, sulfur, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR⁺ (as in N-substituted pyrrolidinyl).

In some embodiments, two independent occurrences of a variable may be taken together with the atom(s) to which each variable is bound to form a 5-8-membered aryl or heteroaryl ring or a 3-8-membered cycloaliphatic ring (e.g., a 4-6-membered cycloalkyl) or heterocyclyl. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, cycloaliphatic or aryl ring, wherein the group is attached to the rest of the molecule by a single point of attachment; and b) two independent occurrences of a substituent that are bound to different atoms and are taken together with both of those atoms to form a heterocyclyl, heteroaryl, cycloaliphatic or aryl ring, wherein the ring that is formed has two points of attachment with the rest of the molecule.

It will be appreciated that a variety of other rings can be formed when two independent occurrences of a substituent are taken together with the atom(s) to which each substituent is bound and that the examples detailed above are not intended to be limiting.

As described herein, a bond drawn from a substituent to the center of one ring within a multiple-ring system (as shown below), represents substitution of the substituent at any substitutable position in any of the rings within the multiple ring system. For example, Formula D3 represents possible substitution in any of the positions shown in Formula D4:

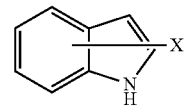

D₃

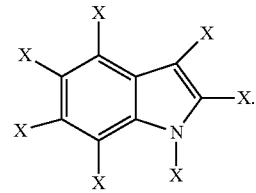

D₄

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

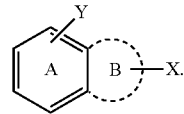

D₆

As used herein, the term "alkoxy" refers to an alkyl group, as previously defined, attached to the molecule, or to another chain or ring, through an oxygen ("alkoxy" i.e., —O-alkyl) atom. The term "alkenoxy" refers to an alkenyl group, as previously defined, attached to the molecule, or to another chain or ring, through an oxygen ("alkenoxy" i.e., —O-alkenyl) atom.

As used herein, the terms "halo", "halogen" and "halide" mean fluorine (F), chlorine (Cl), bromine (Br) or iodine (I).

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH₂CHF₂ and a $C_{1-2}$ haloalkoxy could be —OC(Br)HCHF₂. This term includes perfluorinated alkyl groups, such as —CF₃ and —CF₂CF₃.

As used herein, the term "cyano" refers to —CN or —C≡N.

The term "hydroxyl" or "hydroxy" refers to —OH.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —$CH_2$—C(O)—$CH_3$. When an "oxo' group is listed as a possible substituent on a ring or another moiety or group (e.g. an alkyl chain) it will be understood that the bond between the oxygen in said oxo group and the ring, or moiety it is attached to will be a double bond, even though sometimes it may be drawn generically with a single line.

As used herein, a "carboxylic acid" is an organic compound containing a carboxyl (—C(═O)—OH) group As used herein, an "activated ester" refers to an ester group that is readily displaced by an amine group or an amidrazone group. For example, the activated ester group consists in a —C(═O)OE' group, wherein —OE' is a good leaving group that can be readily displaced. For example, —OE' is selected from —O—($CH_2CF_3$), —O-(nitrophenyl) (e.g, 2 or 4-nitrophenyl), —O-(dinitrophenyl) (e.g. 2,4-dinitrophenyl ester), —O-(trichlorophenyl) (e.g., 2,4,5-trichlorophenyl), —O-(pentafluorophenyl), —O-(sulfo-tetrafluorophenyl) (e.g., 4-sulfo-2,3,5,6-tetrafluorophenyl), —O-(succinimidyl), —O-(benzotriazole), —O-(7-azabenzotriazole), —O-(phthalimidyl), —O-(5-norbornene-endo-2,3-dicarboxyimide), or —O-(sulfo-succinimidyl). In particular, —OE' is —O—($CH_2CF_3$). In one embodiment, the activated ester is $CF_3$C(═O)O$CH_2CF_3$.

As used herein, a thioester" refers to a thioester group that is readily displaced by an amine group or an amidrazone group. For example, the thioester group consists in a —C(═O)SR' group, wherein —SR' is a good leaving group that can be readily displaced.

As used herein, an "acid halide" is an organic compound containing a —C(═O)—X, wherein X is a halogen.

As used herein, a "thioacyl halide" is an organic compound containing a —C(═S)—X, wherein X is a halogen.

As used herein, an "acid anhydride" is an organic compound having two acyl groups bonded to the same oxygen atom. Also included are mixed anhydride in which one of the two acyl groups is derived from phosphoric acid, phosphonic acid or oxime group.

As used herein, an "amidrazone" is an organic compound containing a —C(═NH)—NH—NH-moiety.

As used herein, a "base" is a compound that donates electrons or hydroxide ions or that accepts protons. Exemplary bases may include, but not limited to, trialkylamine (e.g., trimethylamine), an alkoxide (e.g., NaOMe), an alkali metal hydroxide (e.g., LiOH, NaOH, or KOH), an alkali earth metal hydroxide, a carbonate, a phosphazene, 1,8-diazabicyclo(5.4.0)undec-7-ene (DBU), 1,5-diazabicyclo[4.3.0]non-5-ene (DBN), guanidine, 1,1,3,3-tetramethylguanidine, optionally substituted pyridine (e.g., 4-dimethylaminopyridine (DMAP)) or 1,4-diazabicyclo[2.2.2]-octane (DABCO). In one embodiment, the base is selected from an amine, amidine, guanidine, a substituted pyridine, or phosphazene base. In particular, the base is an amine, amidine, guanidine, or a substituted pyridine base and is selected from a trialkylamine (e.g., trimethylamine), 1,8-diazabicyclo(5.4.0)undec-7-ene (DBU), 1,5-diazabicyclo[4.3.0]non-5-ene (DBN), guanidine, 1,1,3,3-tetramethylguanidine, optionally substituted pyridine (e.g., 4-dimethylaminopyridine (DMAP)) or 1,4-diazabicyclo[2.2.2]-octane (DABCO). In one embodiment, the base is selected from trialkylamine, a carbonate, a phosphazene, 1,8-diazabicyclo(5.4.0)undec-7-ene (DBU), 1,5-diazabicyclo[4.3.0]non-5-ene (DBN), guanidine, 1,1,3,3-tetramethylguanidine, optionally substituted pyridine or 1,4-diazabicyclo[2.2.2]-octane (DABCO). In one embodiment, the base is DMAP. In another embodiment, the base is DABCO.

In addition, exemplary bases may include alkali hydroxide (e.g., NaOH, KOH and LiOH), alkali alkoxide (e.g., NaOMe, NaOEt, KOMe and KOEt). In one embodiment, the second base is selected from trialkylamine (e.g., trimethylamine), an alkoxide (e.g., NaOMe, NaOMe, NaOEt, KOMe, KOEt, potassium tert-butoxide), an alkali metal hydroxide (e.g., LiOH, NaOH, or KOH), an alkali earth metal hydroxide, and a carbonate (e.g., calcium carbonate, cesium carbonate, potassium carbonate). In one embodiment, the second base is NaOMe. In another embodiment, the second base is KOMe.

The term "protecting group" or "protecting moiety" refers to a substituent that is commonly employed to block or protect a particular functionality while reacting other functional groups on the compound, a derivative thereof, or a conjugate thereof. For example, an "amidrazone protecting group" is a substituent attached to the amidrazone —NH— group that blocks or protects the amidrazone functionality in the compound. Commonly used amino protecting groups can be used as an amidrazone protecting groups. Such amino protecting groups are also well known in the art (see for example P. Wuts and T. Greene, 2007, Protective Groups in Organic Synthesis, Chapter 7, J. Wiley & Sons, NJ). Suitable amidrazone-protecting groups include, but are not limited to, carbamate amino protecting group, amide amino protecting group, or sulfonyl amino protecting group. For example, the amidrazone-protecting group is selected from the group consisting of tert-butoxycarbonyl (Boc), 2,2,2-trichloroethyloxycarbonyl (Troc), benzyloxycarbonyl (Cbz), 9-fluorenylmethoxycarbonyl (Fmoc), methyl sulfonyl, p-toluenesulfonyl (Tos), 4-nitrobenzenesulfonyl (NOSyl), 2-nitrobenzenesulfonyl, p-bromobenzenesulfonyl (Brosyl), trifluoroacetyl, acetyl, benzoyl, 2-trimethylsilylethyl, (2-phenyl-2-trimethylsilyl)ethyl, triisopropylsiloxy, 2-(trimethylsilyl)ethoxymethyl, allyloxycarbonyl, and 2-(trimethylsilyl)ethoxycarbonyl. For a general description of protecting groups and their use, see P. G. M. Wuts & T. W. Greene, Protective Groups in Organic Synthesis, John Wiley & Sons, New York, 2007.

As used herein, the term "amidrazone deprotecting agent" refers to a reagent that is capable of cleaving an amidrazone protecting group to form free amidrazone. Commonly used amine deprotecting agent can be used as amidazone deprotecting agent. Such amine deprotecting agents are well known in the art (see for example P. Wuts and T. Greene, 2007, Protective Groups in Organic Synthesis, Chapter 2, J. Wiley & Sons, NJ). In some embodiments, an amidrazone deprotecting agent is selected from an acid, a fluorine-containing agent, a silicon-containing agent, and a metal-containing agent, and an amine. Examples of the metal in the metal-containing agent are zinc, cadmium, nickel, palladium, cobalt, aluminum, and mercury, etc. Examples of such amidrazone deprotecting agents include, but are not limited to, tetra-n-butylammonium fluoride, tris(dimethylamino) sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, periodic acid, piperidine, morpholine, pyridine, hydrazine, trimethylsily iodide, phosphoric acid, and trifluoroacetic acid. In certain embodiments, the amidrazone deprotecting agent is selected from tetra-n-butylammonium fluoride, acetic acid, hydrogen fluoride pyridine, cesium fluoride, piperidine, morpholine, pyridine, hydrazine, trimethylsilyl iodide, and trifluoroacetic acid.

As used herein, an "activating agent" refers a reagent or moieties that increase the reactivity of the amidrazone group, increases the reactivity of a carbonyl group and/or activates the hydroxyl group to facilite the coupling reaction between a carboxylic acid and amidrazone group. Examples of such activating agents or moieties include a carbodiimide, a uronium, an active ester, a phosphonium, 2-alkyl-1-alkyl-carbonyl-1,2-dihydroquinoline, 2-alkoxy-1-alkoxycarbonyl-1,2-dihydroquinoline, ethyl cyanohydroxyiminoacetate (Oxyma®), and alkylchloroformate. In a specific embodiment, the activating agent is a carbodiimide. In a more specific embodiment, the activating agent is dicyclohexylcarbodiimide (DCC), 1-ethyl-3-(3-dimethylaminopropyl) carbodiimide (EDC), or diisopropylcarbodiimide (DIC). In another specific embodiment, the activating agent is N-ethoxycarbonyl-2-ethoxy-1,2-dihydroquinoline. In another embodiment, the activating agent is selected from ethylchloroformate and 2-ethoxy-1-ethoxycarbonyl-1,2-dihydroquinoline (EDDQ). In another embodiment, the activating agent is a uronium, such as O-(1H-benzotriazol-1-yl)-N,N,N',N'-tetramethyluronium hexafluorophosphate (HBTU) or its tetrafluroborate equivalent TBTU.

The term "salt" as used herein, refers to an organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A salt may involve the inclusion of another molecule such as an acetate ion, a succinate ion or other counter ion. The counter ion may be any organic or inorganic moiety that stabilizes the charge on the parent compound. Furthermore, a salt may have more than one charged atom in its structure. Instances where multiple charged atoms are part of the salt can have multiple counter ions. Hence, a salt can have one or more charged atoms and/or one or more counter ion.

The term "leaving group" refers to a group of charged or uncharged moiety that departs during a nucleophilic or electrophilic substitution or displacement. Such leaving groups are well known in the art and include, but not limited to, halogens, esters, oxime esters, alkoxy, hydroxyl, tosylates, triflates, mesylates, nitriles, azide, carbamate, disulfides, thioesters, thioethers and diazonium compounds.

Methods of the Present Invention

The present invention provides novel methods for preparing 3-substituted 1,2,4-triazole compounds.

In the first aspect, a second embodiment is a process of preparing a 3-substituted 1,2,4-triazole compound represented by Formula IB:

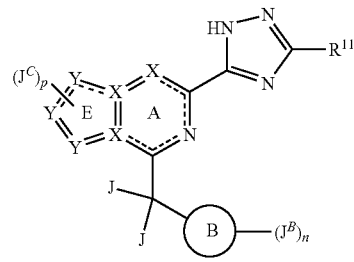

(IB)

or a salt thereof. The process comprises reacting the amidrazone compound represented by Formula IIB:

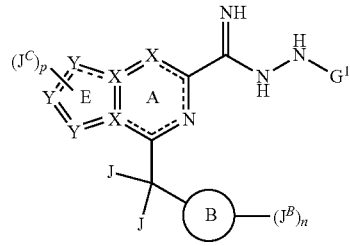

(IIB)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. The values of the variables in Formula IB, Formula IIB, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first embodiment of the first aspect.

In the first aspect, a third embodiment is a process of preparing a 3-substituted 1,2,4-triazole compound represented by Formula IC:

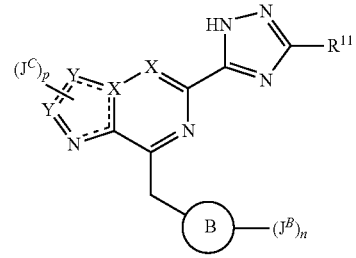

(IC)

or a salt thereof. The process comprises reacting the amidrazone compound represented by Formula IIC:

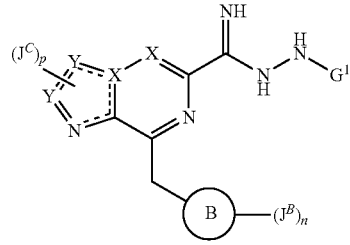

(IIC)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. The values of the variables in Formula IC, Formula IIC, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first embodiment of the first aspect.

In the first aspect, a fourth embodiment is a process of preparing a 3-substituted 1,2,4-triazole compound represented by Formula ID:

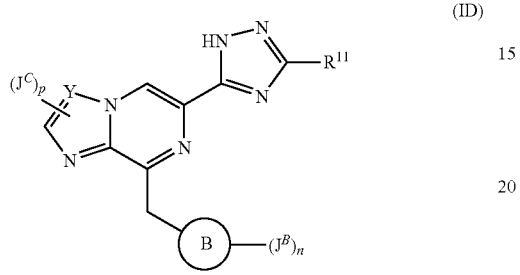

(ID)

or a salt thereof. The process comprises reacting the amidrazone compound represented by Formula IID:

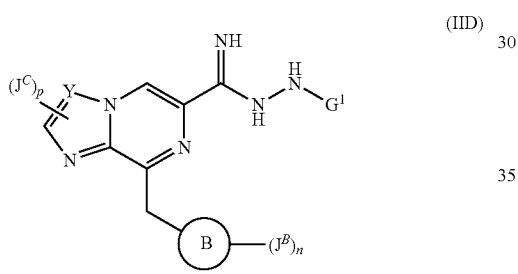

(IID)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. In this embodiment, Y in Formula ID and Formula IID is N or C; and the values of the other variables in Formula ID, Formula IID, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first embodiment of the first aspect.

In the first aspect, a fifth embodiment is a process of preparing a 3-substituted 1,2,4-triazole compound represented by Formula IE:

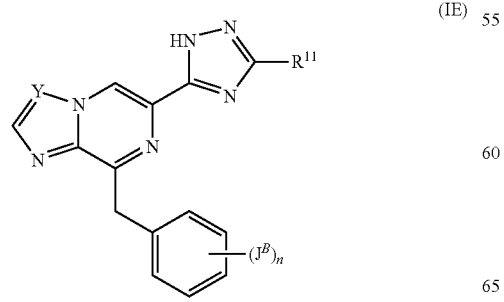

(IE)

or a salt thereof. The process comprises reacting the amidrazone compound represented by Formula IIE:

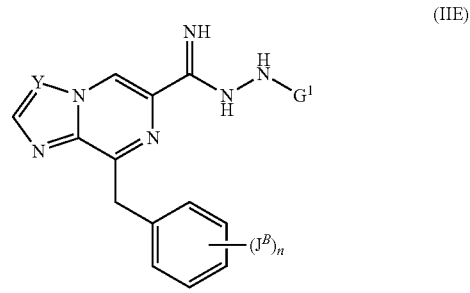

(IIE)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. In this embodiment, the values of the variables in Formula IE, Formula IIE, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first and/or fourth embodiments of the first aspect.

In the first aspect, a sixth embodiment is a process of preparing a 3-substituted 1,2,4-triazole compound represented by Formula IF:

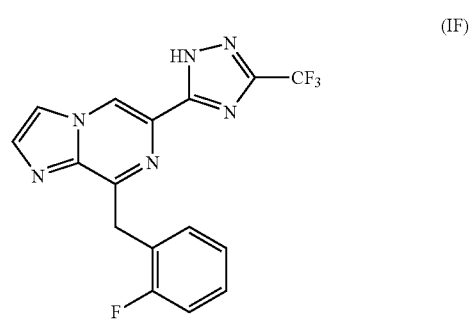 [SMILES: Fc1ccccc1Cc1nc(-c2nc(C(F)(F)F)n[nH]2)cn2ccnc12]

(IF)

or a salt thereof. The process comprises reacting the amidrazone compound represented by Formula IIF:

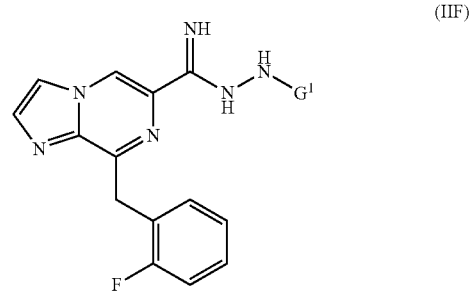

(IIF)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. In this embodiment, $R^{11}$ is $CF_3$ and the values of the other variables in Formula IIF, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first embodiment of the first aspect.

In the first aspect, a seventh embodiment is a process of preparing a 3-substituted 1,2,4-triazole compound represented by Formula IG:

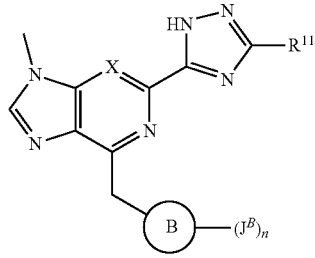

(IG)

or a salt thereof. The process comprises reacting the amidrazone compound represented by Formula IIG:

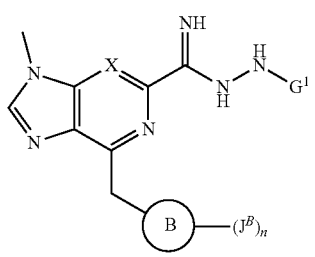

(IIG)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. In this embodiment, X is C or N; and the values of the other variables in Formula IG, Formula IIG, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first embodiment of the first aspect.

In the first aspect, an eighth embodiment is a process of preparing a 3-substituted 1,2,4-triazole compound represented by Formula IH:

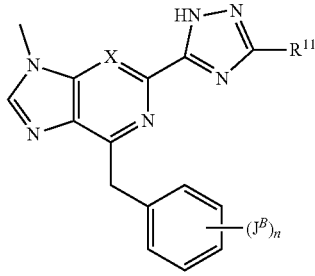

(IH)

or a salt thereof. The process comprises reacting the amidrazone compound represented by Formula IIH:

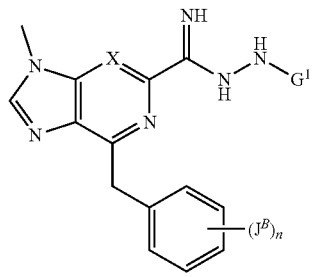

(IIH)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. In this embodiment, the values of the variables in Formula IH, Formula IIH, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first and/or seventh embodiments of the first aspect.

In the first aspect, a nineth embodiment is a process of preparing a 3-substituted 1,2,4-triazole compound represented by Formula IJ:

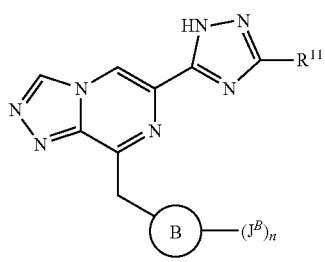

(IJ)

or a salt thereof. The process comprises reacting the amidrazone compound represented by Formula IIJ:

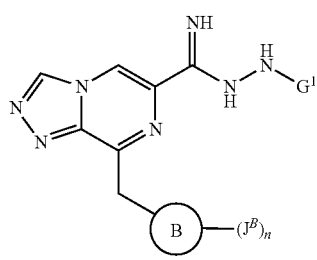

(IIJ)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. In this embodiment, the values of the variables in Formula IJ, Formula IIJ, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first embodiment of the first aspect.

In the first aspect, a tenth embodiment is a process of preparing a 3-substituted 1,2,4-triazole compound represented by Formula IL:

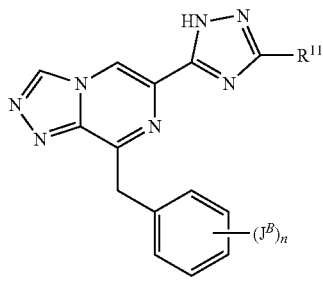

(IL)

or a salt thereof. The process comprises reacting the amidrazone compound represented by Formula IIL:

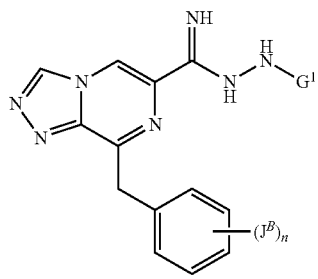

(IIL)

or a salt thereof, in the presence of a base with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. In this embodiment, the values of the variables in Formula IL, Formula IIL, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first embodiment of the first aspect.

In the first aspect, an eleventh embodiment is a process of preparing the 3-substituted 1,2,4-triazole compound represented by Formula IA, IB, IC, ID, IG, IJ or a salt thereof as described in the first, second, third, fourth, seventh or nineth embodiment of the first aspect. Ring B in Formulae IA, IIA, IB, IIB, IC, IIC, ID, IID, IG, IIG, IJ and IIJ is phenyl or a 5 or 6-membered heteroaryl ring, containing 1 or 2 ring nitrogen atoms and the values of the other variables are as defined for the first, fourth and/or seventh embodiments of the first aspect.

In the first aspect, a twelfth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect. $J^B$, $J^C$, p and $R^{11}$ in Formulae IA, IIA, IB, IIB, IC, IIC, ID, IID, IE, IIE, IF, IIF, IG, IIG, IH, IIH, IJ, IIJ, IL and IIL, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are further defined as follows:

$J^B$ is independently halo or a $C_{1-6}$ alkyl optionally substituted with up to 3 instances of halo;

each $J^C$, when present, is independently selected from hydrogen, halo, —CN, and $C_{1-4}$ alkyl optionally and independently substituted by up to 3 instances of halo;

p, when present, is 1 or 2;

$R^{11}$ is H, —$NR^{a2}R^{b2}$, —$C(O)NR^{a2}R^{b2}$, —$C(O)R^{15a}$, —CN, $C_{1-6}$ alkyl optionally and independently substituted with 0-3 occurrences of $R^{15}$, $C_{2-6}$ alkenyl optionally and independently substituted with 0-2 occurrences of $R^{b2}$, $C_{2-6}$ alkynyl optionally and independently substituted with 0-2 occurrences of $R^{b2}$; $C_{1-6}$ alkoxy optionally and independently substituted with 0-5 occurrences of $R^{15}$, phenyl optionally and independently substituted with 0-3 occurrences of $R^{15}$, 5- to 6-membered heteroaryl optionally and independently substituted with 0-3 occurrences of $R^{15}$, $C_{3-8}$ cycloalkyl optionally and independently substituted with 0-3 occurrences of $R^{15}$ or 3-8 membered heterocyclyl optionally and independently substituted with 0-3 occurrences of $R^{15}$; wherein each of said 5- to 6-membered heteroaryl and each of said 3-8 membered heterocyclyl contain up to 3 ring heteroatoms independently selected from N, O or S;

$R^{15}$ is halo, —$OR^{b2}$, —$SR^{b2}$, —$NR^{a2}R^{b2}$, —$C(O)R^{b2}$, —$C(O)NR^{a2}R^{b2}$, —$NR^{b2}C(O)OR^{b2}$, —$OC(O)NR^{a2}R^{b2}$, $C_{2-4}$ alkenoxy, $C_{3-8}$ cycloalkyl, phenyl, 5- or 6-membered heteroaryl, or 3-10 membered heterocyclyl; wherein each of said 5- or 6-membered heteroaryl ring and each of said 3-10 membered heterocyclyl contain up to 3 ring heteroatoms independently selected from N, O or S;

$R^{15a}$ is $C_{3-8}$ cycloalkyl, phenyl, 5- or 6-membered or 3-10 membered heterocyclyl; wherein each of said 5- or 6-membered heteroaryl ring and each of said 3-10 membered heterocyclyl contain up to 3 ring heteroatoms independently selected from N, O or S; and $R^{a2}$ is hydrogen, $C_{1-6}$ alkyl or $C_{1-6}$ haloalkyl; and $R^{b2}$ is hydrogen, $C_{1-6}$ alkyl or $C_{1-6}$ haloalkyl.

The values of the other variables in Formulae IA, IIA, IB, IIB, IC, IIC, ID, IID, IE, IIE, IF, IIF, IG, IIG, IH, IIH, IJ, IIJ, IL and IIL, $R^{11}C(O)X'$, $R^{11}C(S)X'$, $R^{11}C(O)OE'$, $R^{11}C(O)SR'$, and $R^{11}C(O)OR''$ are as defined for the first, fourth, seventh and/or eleventh embodiments of the first aspect.

In the first aspect, a thirteenth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect. $R^{11}$ in Formulae IA, IB, IC, ID, IE, IF, IG, IH, IJ and IL, $R^{11}C(O)OH$ $R^{11}C(O)X'$, $R^{11}C(S)X'$, $R^{11}C(O)OE'$, $R^{11}C(O)SR'$, and $R^{11}C(O)OR''$ is —$NR^{a2}R^{b2}$, $C_{1-6}$ alkyl optionally and independently substituted with 0-3 occurrences of halo, 5- to 6-membered heteroaryl optionally and independently substituted with 0-3 occurrences of halo, or $C_{3-8}$ cycloalkyl optionally and independently substituted with 0-3 occurrences of halo. $J^B$ and $J^C$ are as defined for the twelfth embodiment of the first aspect. The values of the other variables in Formulae IA, IIA, IB, IIB, IC, IIC, ID, IID, IE, IIE, IF, IIF, IG, IIG, IH, IIH, IJ, IIJ, IL and IIL, $R^{11}C(O)X'$, $R^{11}C(S)X'$, $R^{11}C(O)OE'$, $R^{11}C(O)SR'$, and $R^{11}C(O)OR''$ are as defined for the first, fourth and/or seventh embodiments of the first aspect.

In the first aspect, a fourteenth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect. $R^H$ in Formulae IA, IB, IC, ID, IE, IF, IG, IH, IJ, and IL, $R^{11}C(O)OH$ $R^{11}C(O)X'$, $R^{11}C(S)X'$, $R^{11}C(O)OE'$, $R^{11}C(O)SR'$, and $R^{11}C(O)OR''$ is $C_{1-6}$ alkyl optionally and independently substituted with 0-3 occurrences of halo. $J^B$ and $J^C$ are as defined for the twelfth embodiment of the first aspect. The values of the other variables in Formulae IA, IIA, IB, IIB, IC, IIC, ID, IID, IE, IIE, IF, IIF, IG, IIG, IH, IIH, IJ, IIJ, IL and IIL, $R^{11}C(O)X'$, $R^{11}C(S)X'$, $R^{11}C(O)OE'$, $R^{11}C(O)SR'$, and $R^{11}C(O)OR''$ are as defined for the first, fourth and/or seventh embodiments of the first aspect.

In the first aspect, a fifteenth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect. $R^{18}$ in Formulae IA, IB, IC, ID, IE, IF, IG, IH, IJ, and IL, $R^{11}C(O)OH$, $R^{11}C(O)X'$, $R^{11}C(S)X'$, $R^{11}C(O)OE'$, $R^{11}C(O)SR'$, and $R^{11}C(O)OR''$ is $CF_3$. $J^B$ and $J^C$ are as defined for the twelfth embodiment of the first aspect. The values of the other variables in Formulae IA, IIA, IB, IIB, IC, IIC, ID, IID, IE, IIE, IF, IIF, IG, IIG, IH, IIH, IJ, IIJ, IL and IIL, $R^{11}C(O)X'$, $R^{11}C(S)X'$, $R^{11}C(O)OE'$, $R^{11}C(O)SR'$, and $R^{11}C(O)OR''$ are as defined for the first, fourth and/or seventh embodiments of the first aspect.

In the first aspect, a sixteenth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect. $G^1$ in Formulae IIA, IIB, IIC, IID, IIE, IIF, IIG, IIH, IIJ and IIL is carbamate amino protecting group, amide amino protecting group, or sulfonyl amino protecting group. The values of the other variables in Formulae IA, IIA, IB, IIB, IC, IIC, ID, IID, IF, IIF, IG, IIG, IH, IIH, IJ, IIJ, IL and IIL, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first, fourth, seventh, eleventh, twelfth, thirteenth, fourteenth and/or fifteenth embodiments of the first aspect.

In the first aspect, a seventeenth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect. $G^1$ in Formulae IIA, IIB, IIC, IID, IIE, IIF, IIG, IIH, IIJ and IIL is tert-butoxycarbonyl (Boc), 2,2,2-trichloroethyloxycarbonyl (Troc), benzyloxycarbonyl (Cbz), 9-Fluorenylmethoxycarbonyl (Fmoc), methylsulfonyl, p-toluenesulfonyl (Tos), 4-nitrobenzenesulfonyl (NOSyl), 2-nitrobenzenesulfonyl, p-bromobenzenesulfonyl (Brosyl), trifluoroacetyl, acetyl or benzoyl. The values of the other variables in Formulae IA, IIA, IB, IIB, IC, IIC, ID, IID, IE, IIE, IF, IIF, IG, IIG, IH, IIH, IJ, IIJ, IL and IIL, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first, fourth, seventh, eleventh, twelfth, thirteenth, fourteenth and/or fifteenth embodiments of the first aspect.

In the first aspect, an eighteenth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IIH, IIJ, IIL or a salt thereof, in the presence of the base, with $R^{11}C(O)OE'$, wherein —OE' is —O—($C_{1-6}$alkyl), —O—($C_{1-6}$haloalkyl), —O-(phenyl), —O-(heteroaryl), —O-(heterocyclyl), wherein the phenyl, heteroaryl, and heterocyclyl are optionally substituted with 1 to 6 groups independently selected from halo, cyano, nitro, oxo, $SO_3H$, and $SO_3C_{1-6}$alkyl. The values of the other variables in Formulae IA, IIA, IB, IIB, IC, IIC, ID, IID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a nineteenth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IIH, IIJ, IIL or a salt thereof, in the presence of the base, with $R^{11}C(O)OE'$, wherein —OE' is —O—($C_{1-6}$haloalkyl). The values of the other variables in Formulae IA, IIA, IB, IIB, IC, IIC, ID, IID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a twentith embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IIH, IIJ, IIL or a salt thereof, in the presence of the base, with $R^{11}C(O)OE'$, wherein —OE' is —O—($CH_2CF_3$), —O-(nitrophenyl) (e.g., 2 or 4-nitrophenyl), —O-(dinitrophenyl) (e.g. 2,4-dinitrophenyl ester), —O-(trichlorophenyl) (e.g., 2,4,5-trichlorophenyl), —O-(pentafluorophenyl), —O-(sulfo-tetrafluorophenyl) (e.g., 4-sulfo-2,3,5,6-tetrafluorophenyl), —O-(succinimidyl), —O-(benzotriazole), —O-(7-azabenzotriazole), —O-(phthalimidyl), —O-(5-norbornene-endo-2,3-dicarboxyimide), or —O-(sulfo-succinimidyl). The values of the other variables in Formulae IA, IIA, IB, IIB, IC, IIC, ID, IID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a twenty-first embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IIH, IIJ, IIL or a salt thereof, in the presence of the base, with $R^{11}C(O)OR''$, wherein R'' is N=$CR^{11b}R^{11c}$, $P(O)(OH)_2$, or $PH(O)OH$. The values of the other variables in Formulae IA, IIA, IB, IIB, IC, IIC, ID, IID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a twenty-second embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IIH, IIJ, IIL or a salt thereof, in the presence of the base, with $R^{11}C(O)OH$ in the presence of an activating agent. The values of the other variables in Formulae IA, IIA, IB, IIB, IC, IIC, ID, IID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a twenty-third embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IIH, IIJ, IIL or a salt thereof, in the presence of the base, with $R^{11}C(O)OH$ in the presence of an activating agent, wherein the activating agent is a carbodiimide, a uronium, a phosphonium, 2-alkyl-1-alkylcarbonyl-1,2-dihydroquinoline, 2-alkoxy-1-alkoxycarbonyl-1,2-dihydroquinoline, ethyl cyanohydroxyiminoacetate (Oxyma®), or alkylchloroformate. The values of the other variables in Formulae IA, IIA, IB, IIB, IC, IIC, ID, IID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a twenty-fourth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, BE, BF, IIG, IIH, IIJ, IIL or a salt thereof, in the presence of the base, with $R^{11}C(O)SR'$, wherein —SR' is —S-(aryl), —S—($C_{1-20}$ alkyl), or —S-(heteroaryl). The values of the other variables in Formulae IA, IIA, IB, IIB, IC, IIC, ID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a twenty-fifth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IH, IIH, IIJ, IIL or a salt thereof, in the presence of the base, with $R^{11}C(O)SR'$, wherein —SR' is —S-(ethyl), —S-(dodecyl), —S-(p-chlorophenyl), or —S-(2-benzothiazolyl). The values of the other variables in Formulae IA, IIA, IB, IIB, IC, IIC, ID, IID, IE, IIE, IF, IIF, IG, IIG, IH, IIH, IJ, IIJ, IL and IIL are as defined for the first, fourth, seventh, eleventh, twelfth, thirteenth, fourteenth, fifteenth, sixteenth and/or seventeenth embodiments of the first aspect.

In the first aspect, a twenty-sixth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IH, IIH, IIJ, IIL or a salt thereof, in the presence of the base, with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present, wherein the base is selected from the group consisting of trialkylamine, a carbonate, a phosphazene, 1,8-diazabicyclo(5.4.0)undec-7-ene (DBU), 1,5-diazabicyclo[4.3.0]non-5-ene (DBN), guanidine, 1,1,3,3-tetramethylguanidine, optionally substituted pyridine or 1,4-diazabicyclo[2.2.2]-octane (DABCO), or in specific embodiment, the base is selected from the group consisting of trialkylamine, a phosphazene, 1,8-diazabicyclo(5.4.0)undec-7-ene (DBU), 1,5-diazabicyclo[4.3.0]non-5-ene (DBN), guanidine, 1,1,3,3-tetramethylguanidine, optionally substituted pyridine or 1,4-diazabicyclo[2.2.2]-octane (DABCO). The values of the variables in Formulae IA, IIA, IB, IIB, IC, IIC, ID, IID, IE, IIE, IF, IIF, IG, IIG, IH, IIH, IJ, IIJ, IL and IIL, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first, fourth, seventh, eleventh, twelfth, thirteenth, fourteenth, fifteenth, sixteenth, seventeenth, eighteenth, nineteenth, twentieth, twenty-first, twenty-second, twenty-third, twenty-fourth and/or twenty-fifth embodiments of the first aspect.

In the first aspect, a twenty-seventh embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the amidrazone compound represented by Formula IIA, IIB, IIC, IID, IIE, IIF, IIG, IIH, IIJ, IIL or a salt thereof, in the presence of the base, with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present, wherein the base is 4-dimethylaminopyridine (DMAP). The values of the variables in Formulae IA, IIA, IB, IIB, IC, IIC, ID, IID, IE, IIE, IF, IIF, IG, IIG, IH, IIH, IJ, IIJ, IL and IIL, $R^{11}C(O)OH$ $R^{11}C(O)X'$, $R^{11}C(S)X'$, $R^{11}C(O)OE'$, $R^{11}C(O)SR'$, and $R^{11}C(O)OR''$ are as defined for the first, fourth, seventh, eleventh, twelfth, thirteenth, fourteenth, fifteenth, sixteenth, seventeenth, eighteenth, nineteenth, twentieth, twenty-first, twenty-second, twenty-third, twenty-fourth and/or twenty-fifth embodiments of the first aspect.

In the first aspect, a twenty-eighth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect, comprising reacting the seventh, eighth, nineth or tenth embodiment of the first aspect, comprising reacting the amidrazone compound represented by Formula IIA, IIB, IIC, IID, IIE, IIF, IIG, IIH, IIJ, IIL, or a salt thereof, in the presence of the base, with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present, wherein the base is DABCO. The values of the variables in Formulae IA, IIA, IB, IIB, IC, IIC, ID, IID, IE, IIE, IF, IIF, IG, IIG, IH, IIH, IJ, IIJ, IL and IIL, $R^{11}C(O)OH$, $R^{11}C(O)X'$, $R^{11}C(S)X'$, $R^{11}C(O)OE'$, $R^{11}C(O)SR'$, and $R^{11}C(O)OR''$ are as defined for the first, fourth, seventh, eleventh, twelfth, thirteenth, fourteenth, fifteenth, sixteenth, seventeenth, eighteenth, nineteenth, twentieth, twenty-first, twenty-second, twenty-third, twenty-fourth and/or twenty-fifth embodiments of the first aspect.

In the first aspect, a twenty-nineth embodiment is a process of preparing the 3-substituted 1,2,4-triazole compound represented by Formula IA, IB, IC, ID, IE, IF, IG, IH, IJ, IL or a salt thereof as described in the first, second, third, fourth, fifth, sixth, seventh, eighth, nineth or tenth embodiment of the first aspect. The process further comprises deprotecting the amidrazone protecting group if necessary after the reaction of the amidrazone compound with the carboxylic acid, the acid halide, the thioacyl halide, the activated ester, the thioester or the acid anhydride by reacting the reaction product with an amidrazone deprotecting agent. The values of the variables in Formulae IA, IIA, IB, IIB, IC, IIC, ID, IID, IE, IIE, IF, IIF, IG, IIG, IH, IIH, IJ, IIJ, IL and IIL, $R^{11}C(O)OH$, $R^{11}C(O)X'$, $R^{11}C(S)X'$, $R^{11}C(O)OE'$, $R^{11}C(O)SR'$, $R^{11}C(O)OR''$, and the base are as defined for the first, fourth, seventh, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh and/or twenty-eighth embodiments of the first aspect.

In the first aspect, a thirtieth embodiment is a process of preparing the 3-substituted 1,2,4-triazole compound represented by Formula IA or a salt thereof as described in the first embodiment of the first aspect, comprising reacting the amidrazone compound represented by Formula IIA or a salt thereof, in the presence of the base, with $R^{11}C(O)OH$, $R^{11}C(O)X'$, $R^{11}C(S)X'$, $R^{11}C(O)OE'$, $R^{11}C(O)SR'$, or $R^{11}C(O)OR''$, wherein when $R^{11}C(O)OH$ is used, an activating agent is also present. The amidrazone compound represented by Formula IIA or a salt thereof is prepared by a process comprising reacting a compound of Formula IIIA:

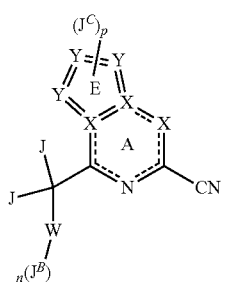

(IIIA)

or a salt thereof, first with a second base and second with a compound of Formula $H_2NNHG^1$ in a reaction solvent. The values of the variables in Formulae IA, IIA, IIIA, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect. In one embodiment, the compound represented by Formula IIIA or a salt thereof is a compound of Formula IIIB:

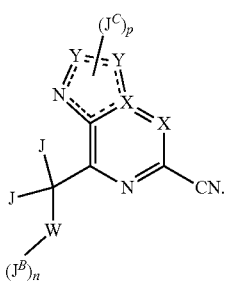

(IIIB)

The values of the variables in Formulae IA, IIA, IIIB, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect. In one embodiment, the compound represented by Formula IIIA or a salt thereof is a compound of Formula IIIC:

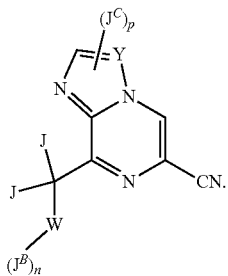

(IIIC)

The values of the variables in Formulae IA, IIA, IIIC, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect. In one aspect, the compound represented by Formula IIIA or a salt thereof is a compound of Formula IIID:

(IIID)

The values of the variables in Formulae IA, IIA, IIID, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect. In one aspect, the compound represented by Formula IIIA or a salt thereof is a compound of Formula IIIE:

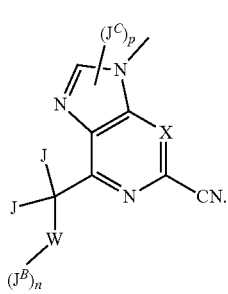

(IIIE)

The values of the variables in Formulae IA, IIA, IIIE, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect. In one aspect, the compound represented by Formula IIIA or a salt thereof is a compound of Formula IIIF:

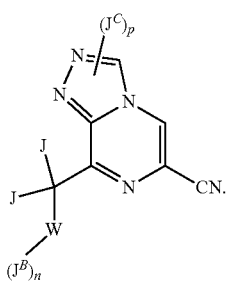

(IIIF)

The values of the variables in Formulae IA, IIA, IIIF, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect. In certain embodiments, for formula IIIA, IIIB, IIIC, IIID, IIIE or IIIF described above, W is a ring B that is phenyl or a 5 or 6-membered heteroaryl ring, containing 1 or 2 ring nitrogen atoms. More specifically, W is a phenyl. In certain embodiments, for formula IIIA, IIIB, IIIC, IIID, IIIE or IIIF described above, $J^B$ is independently halo or a C1-6 alkyl optionally substituted with up to 3 instances of halo; each $J^C$, when present, is independently selected from hydrogen, halo, —CN, and C1-4 alkyl optionally and independently substituted by up to 3 instances of halo; and p, when present, is 1 or 2.

In the first aspect, a thirty-first embodiment is a process of preparing the 3-substituted 1,2,4-triazole compound represented by Formula IA or a salt thereof as described in the first embodiment of the first aspect, comprising reacting the amidrazone compound represented by Formula IIA or a salt thereof, in the presence of the base, with $R^{11}C(O)OH$, $R^{11}C(O)X'$, $R^{11}C(S)X'$, $R^{11}C(O)OE'$, $R^{11}C(O)SR'$, $R^{11}C(O)OR''$, wherein when $R^{11}C(O)OH$ is used, an activating agent is also present. The amidrazone compound represented by Formula IIA or a salt thereof is prepared as described in the thirtieth embodiment, comprising reacting the compound of Formula IIIA first with a second base and second with a compound of Formula $H_2NNHG^1$ in a reaction solvent, wherein the reaction solvent is an alcohol. The values of the variables in Formulae IA, IIA, IIIA, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect.

In the first aspect, a thirty-second embodiment is a process of preparing the 3-substituted 1,2,4-triazole compound represented by Formula IA or a salt thereof as described in the first embodiment of the first aspect, comprising reacting the amidrazone compound represented by Formula IIA or a salt thereof, in the presence of the base, with $R^{11}C(O)OH$, $R^{11}C(O)X'$, $R^{11}C(S)X'$, $R^{11}C(O)OE'$, $R^{11}C(O)SR'$, $R^{11}C(O)OR''$, wherein when $R^{11}C(O)OH$ is used, an activating agent is also present. The amidrazone compound represented by Formula IIA or a salt thereof is prepared as described in the thirtieth embodiment, comprising reacting the compound of Formula IIIA first with a second base and second with a compound of Formula $H_2NNHG^1$ in a reaction solvent, wherein the reaction solvent is MeOH. The values of the variables in Formulae IA, IIA, IIIA, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect.

In the first aspect, a thirty-third embodiment is a process of preparing the 3-substituted 1,2,4-triazole compound represented by Formula IA or a salt thereof as described in the first embodiment of the first aspect, comprising reacting the amidrazone compound represented by Formula IIA or a salt thereof, in the presence of the base, with $R^{11}C(O)OH$, $R^{11}C(O)X'$, $R^{11}C(S)X'$, $R^{11}C(O)OE'$, $R^{11}C(O)SR'$, $R^{11}C(O)OR''$, wherein when $R^{11}C(O)OH$ is used, an activating agent is also present. The amidrazone compound represented by Formula IIA or a salt thereof is prepared as described in the thirtieth, thirty-first, thirty-second embodiment, comprising reacting the compound of Formula IIIA first with a second base and second with a compound of Formula $H_2NNHG^1$ in the reaction solvent, wherein the second base is NaOMe. The values of the variables in Formulae IA, IIA, IIIA, $R^{11}C(O)OH$, $R^{11}C(O)X'$, $R^{11}C(S)X'$, $R^{11}C(O)OE'$, $R^{11}C(O)SR'$, $R^{11}C(O)OR''$, and $H_2NNHG^1$ are as defined for the first embodiment of the first aspect.

In the first aspect, a thirty-fourth embodiment is a process of preparing the 3-substituted 1,2,4-triazole compound represented by Formula IA or a salt thereof as described in the first embodiment of the first aspect, comprising reacting the amidrazone compound represented by Formula IIA or a salt thereof, in the presence of the base, with $R^{11}C(O)OH$, $R^{11}C(O)X'$, $R^{11}C(S)X'$, $R^{11}C(O)OE'$, $R^{11}C(O)SR'$, $R^{11}C(O)OR''$, wherein when $R^{11}C(O)OH$ is used, an activating agent is also present. The amidrazone compound represented by Formula IIA or a salt thereof is prepared as described in the thirtieth, thirty-first, thirty-second, or thirty-third embodiment, the compound of Formula $H_2NNHG^1$ is $H_2NNHC(O)OC(CH_3)_3$, $H_2NNHC(O)OCH_2CCl_3$, $H_2NNHC(O)Obenzyl$, $H_2NNHC(O)OCH_2$(9-fluorenyl), $NH_2NHSO_2CH_3$, $NH_2NHSO_2$(p-toluene), $NH_2NHSO_2$(4-nitrophenyl), $NH_2NHSO_2$(2-nitrophenyl), $NH_2NHSO_2$(4-bromophenyl), $NH_2NHC(O)CF_3$, $H_2NNHC(O)phenyl$ or $H_2NNHC(O)CH_3$. The values of the variables in Formulae IA, IIA, IIIA, $R^{11}C(O)OH$, $R^{11}C(O)X'$, $R^{11}C(S)X'$, $R^{11}C(O)OE'$, $R^{11}C(O)SR'$ and $R^{11}C(O)OR''$ are as defined for the first embodiment of the first aspect.

In the first aspect, a thirty-fifth embodiment is a process of preparing a 3-substituted 1,2,4-triazole compound represented by Formula IF:

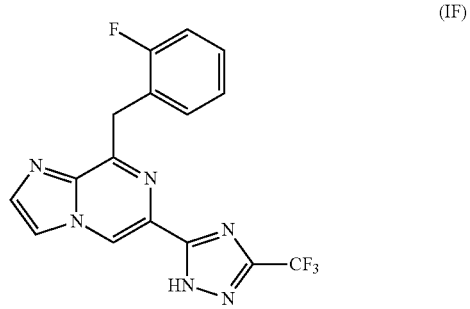 [SMILES: Fc1ccccc1Cc1nc(-c2nc(C(F)(F)F)n[nH]2)cn2ccnc12]

(IF)

or a salt thereof. The process comprises reacting an amidrazone represented by Formula IIFa:

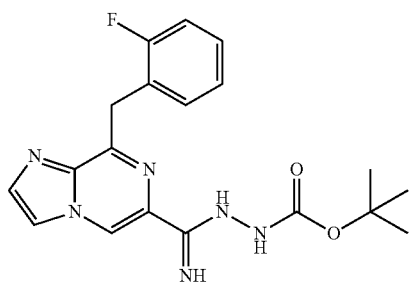

(IIFa)

or a salt thereof, in the presence of a base with CF$_3$C(O)OCH$_2$CF$_3$.

In the first aspect, a thirty-sixth embodiment is a process of preparing the 3-substituted 1,2,4-triazole compound represented by Formula IF or a salt thereof as described in the thirty-fifth embodiment of the first aspect. The base is DABCO.

In the first aspect, a thirty-seventh embodiment is a process of preparing the 3-substituted 1,2,4-triazole compound represented by Formula IF or a salt thereof as described in the thirty-fifth or thirty-sixth embodiment of the first aspect. The process further comprises purifying the 3-substituted 1,2,4-triazole compound of formula IF by crystallization.

In the first aspect, a thirty-eighth embodiment is a process of preparing the 3-substituted 1,2,4-triazole compound represented by Formula IF or a salt thereof as described in the thirty-fifth or thirty-sixth embodiment of the first aspect. The process further comprises purifying the 3-substituted 1,2,4-triazole compound of formula IF by crystallization, wherein the crystallization is carried out by adding n-heptane to the reaction mixture after the completion of the reaction between the amidrazone compound represented by Formula IIFa and CF$_3$C(O)OCH$_2$CF$_3$.

In the first aspect, a thirty-ninth embodiment is a process of preparing the 3-substituted 1,2,4-triazole compound represented by Formula IF or a salt thereof as described in the thirty-fifth, thirty-sixth, thirty-seventh or thirty-eighth embodiment of the first aspect, comprising reacting the amidrazone compound represented by Formula IIFa or a salt thereof, in the presence of the base, with CF$_3$C(O)OCH$_2$CF$_3$. The amidrazone compound represented by Formula IIFa or a salt thereof is prepared by a process comprising reacting a compound of Formula IIIFa:

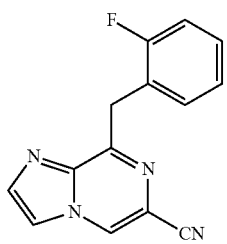

(IIIFa)

or a salt thereof, first with a second base and second with a compound of H$_2$NNHC(O)OC(CH$_3$)$_3$ in a reaction solvent.

In the first aspect, a fortieth embodiment is a process of preparing the 3-substituted 1,2,4-triazole compound represented by Formula IF or a salt thereof as described in the thirty-fifth, thirty-sixth, thirty-seventh or thirty-eighth embodiment of the first aspect, comprising reacting the amidrazone compound represented by Formula IIFa or a salt thereof, in the presence of the base, with CF$_3$C(O)OCH$_2$CF$_3$. The amidrazone compound represented by Formula IIFa or a salt thereof is prepared by a process as described in the thirty-nineth embodiment, comprising reacting the compound of Formula IIIFa or a salt thereof first with the second base and second with H$_2$NNHC(O)OC(CH$_3$)$_3$ in a reaction solvent, wherein the reaction solvent is an alcohol.

In the first aspect, a forty-first embodiment is a process of preparing the 3-substituted 1,2,4-triazole compound represented by Formula IF or a salt thereof as described in the thirty-fifth, thirty-sixth, thirty-seventh or thirty-eighth embodiment of the first aspect, comprising reacting the amidrazone compound represented by Formula IIFa or a salt thereof, in the presence of the base, with CF$_3$C(O)OCH$_2$CF$_3$. The amidrazone compound represented by Formula IIFa or a salt thereof is prepared by a process as described in the thirty-nineth embodiment, comprising reacting the compound of Formula IIIFa or a salt thereof first with the second base and second with H$_2$NNHC(O)OC(CH$_3$)$_3$ in a reaction solvent, wherein the reaction solvent is MeOH.

In the first aspect, a forty-second embodiment is a process of preparing the 3-substituted 1,2,4-triazole compound represented by Formula IF or a salt thereof as described in the thirty-fifth, thirty-sixth, thirty-seventh or thirty-eighth embodiment of the first aspect, comprising reacting the amidrazone compound represented by Formula IIFa or a salt thereof, in the presence of the base, with CF$_3$C(O)OCH$_2$CF$_3$. The amidrazone compound represented by Formula IIFa or a salt thereof is prepared by a process as described in the thirty-nineth, fortieth or forty-first embodiment, comprising reacting the compound of Formula IIIFa or a salt thereof first with the second base and second with H$_2$NNHC(O)OC(CH$_3$)$_3$ in the reaction solvent, wherein the second base is NaOMe.

Any suitable organic solvents may be used for the reactions described herein. Exemplary solvents include, but are not limited to, dimethylformamide (DMF), dichloromethane (DCM), dichloroethane, tetrahydrofuran (THF), dimethylacetamide (DMA), ethylacetate, isopropyl acetate (IPAC), methanol, ethanol, acetonitrile, acetone etc.

In one embodiment, the reaction between the amidrazone compound and R$^{11}$C(O)OH, R$^{11}$C(O)X', R$^{11}$C(S)X', R$^{11}$C(O)OE', R$^{11}$C(O)SR', or R$^{11}$C(O)OR" is carried out in IPAC.

In some embodiments, the 3-substituted 1,2,4-triazole compound represented by Formula IA, IB, IC, ID, IE, IF, IG, IH, IJ, IL or a salt thereof is purified by crystallization. In one embodiment, crystallization is carried out by adding a co-solvent to a solution comprising the 3-substituted 1,2,4-triazole compound.

As used herein, a "co-solvent" refers to a solvent in which the 3-substituted 1,2,4-triazole compound is insoluble or has low solubility. Exemplary co-solvents include, but are not limited to, heptane, hexane, cyclohexane, toluene, etc.

Compounds of the Invention

In a second embodiment of the second aspect, the compound is represented by Formula IIB:

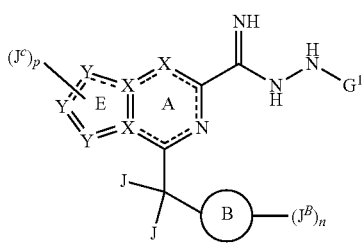

(IIB)

or a salt thereof, wherein the values of the variables are as defined for the first embodiment of the second aspect.

In a third embodiment of the second aspect, the compound is represented by Formula IIC:

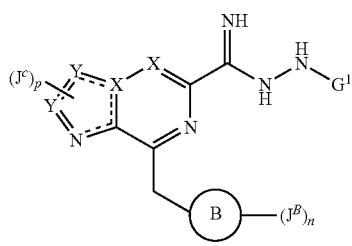

(IIC)

or a salt thereof, wherein the values of the variables are as defined for the first embodiment of the second aspect.

In a fourth embodiment of the second aspect, the compound is represented by Formula IID:

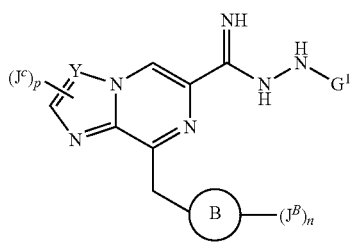

(IID)

or a salt thereof, wherein Y is N or C; and the values of the other variables are as defined for the first embodiment of the second aspect.

In a fifth embodiment of the second aspect, the compound is represented by Formula IIE:

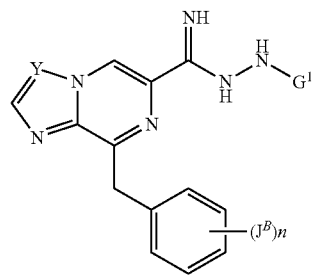

(IIE)

or a salt thereof, wherein the values of the variables are as defined for the first and/or fourth embodiments of the second aspect.

In a sixth embodiment of the second aspect, the compound is represented by Formula IIF:

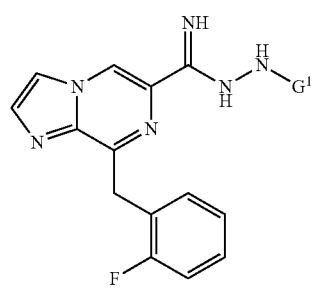

(IIF)

or a salt thereof, wherein the values of the variables are as defined for the first embodiment of the second aspect.

In a seventh embodiment of the second aspect, the compound is represented by Formula IIG:

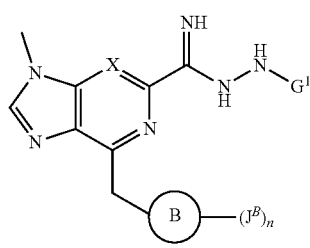

(IIG)

or a salt thereof, wherein X is C or N; and the values of the other variables are as defined for the first embodiment of the second aspect.

In an eighth embodiment of the second aspect, the compound is represented by Formula IIH:

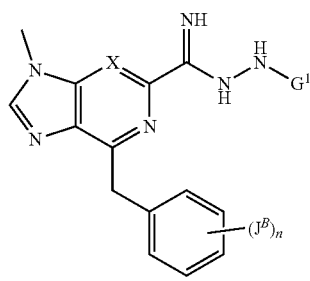

(IIH)

or a salt thereof, wherein the values of the variables are as defined for the first and/or seventh embodiments of the second aspect.

In a ninth embodiment of the second aspect, the compound is represented by Formula III:

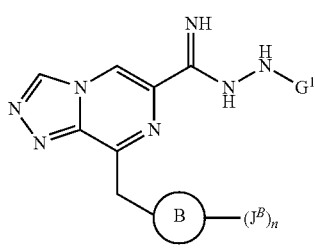

(IIJ)

or a salt thereof, wherein the values of the variables are as defined for the first embodiment of the second aspect.

In a tenth embodiment of the second aspect, the compound is represented by Formula IIL:

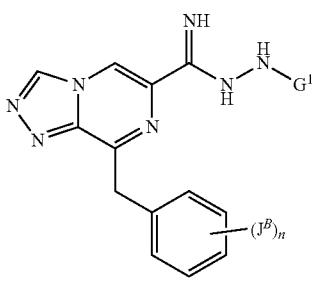

(IIL)

or a salt thereof,
wherein the values of the variables are as defined for the first embodiment of the second aspect.

In an eleventh embodiment of the second aspect, the compound is represented by formula IIA, IIB, IIC, IID, IIG, IIJ or a salt thereof, wherein Ring B is phenyl or a 5 or 6-membered heteroaryl ring, containing 1 or 2 ring nitrogen atoms; and wherein the values of the other variables are as defined for the first, fourth and/or seventh embodiments of the second aspect.

In a twelfth embodiment of the second aspect, the compound is represented by formula IIA, IIB, IIC, IID, IIE, IIF, IIG, IIH, IIJ, IIL or a salt thereof, wherein $J^B$ is independently halo or a $C_{1-6}$ alkyl optionally substituted with up to 3 instances of halo;

each $J^C$, when present, is independently selected from hydrogen, halo, —CN, or $C_{1-4}$ alkyl optionally and independently substituted by up to 3 instances of halo; and p, when present, is 1 or 2; and
wherein the values of the other variables are as defined for the first, fourth, seventh and/or eleventh embodiments of the second aspect.

In a thirteenth embodiment of the second aspect, the compound is represented by formula IIA, IIB, IIC, IID, IIE, IIF, IIG, IIH, IIJ, IIL or a salt thereof, wherein $G^1$ is carbamate amino protecting group, amide amino protecting group, or sulfonyl amino protecting group; and wherein the values of the other variables are as defined for the first, fourth, seventh, eleventh and/or twelfth embodiments of the second aspect.

In a fourteenth embodiment of the second aspect, the compound is represented by formula IIA, IIB, IIC, IID, IIE, IIF, IIG, IIH, IIJ, IIL or a salt thereof, wherein $G^1$ is tert-butoxycarbonyl (Boc), 2,2,2-trichloroethyloxycarbonyl (Troc), benzyloxycarbonyl (Z), 9-Fluorenylmethoxycarbonyl (Fmoc), methyl sulfonyl, p-toluenesulfonyl (Tos), 4-nitrobenzenesulfonyl (NOSyl), 2-nitrobenzenesulfonyl, p-bromobenzenesulfonyl (Brosyl), trifluoroacetyl, acetyl or benzoyl; and wherein the values of the other variables are as defined for the first, fourth, seventh, eleventh and/or twelfth embodiments of the second aspect.

In a fifteenth embodiment of the second aspect, the compound is represented by Formula IIFa:

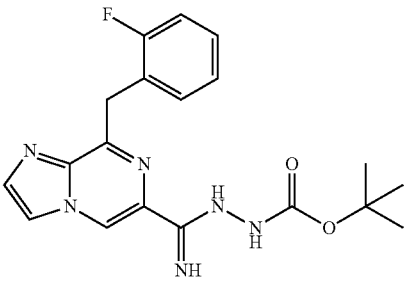

(IIFa)

or a salt thereof.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, 2$^{nd}$ Ed., Washington, D.C.: American Chemical Society, 1997, herein incorporated in its entirety by reference.

Example 1

Synthesis of 8-(2-Fluorobenzyl)imidazo[1,2-a]pyrazine-6-carbonitrile (Nitrile)

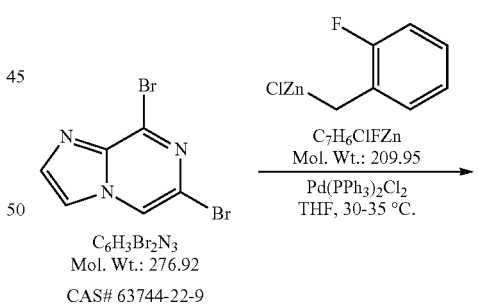

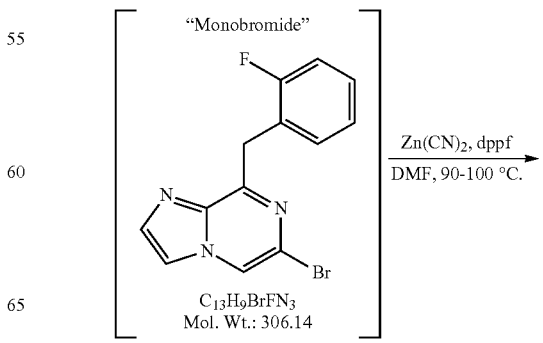

-continued

"Nitrile"

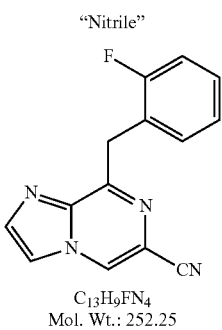

C$_{13}$H$_9$FN$_4$
Mol. Wt.: 252.25

The title compound was synthesized in 2 steps according to a patent literature procedure (WO2015/187470A1) as a yellow solid (0.60 g, 39% yield over 2 steps). $^1$H NMR (500 MHz, Methanol-d$_4$) δ (ppm) 9.09 (s, 1H), 8.14 (s, 1H), 7.91 (s, 1H), 7.35 (t, 1H), 7.28 (m, 1H), 7.10 (m, 2H), 4.60 (s, 2H).

Synthesis of tert-butyl 2-((8-(2-fluorobenzyl)imidazo[1,2-a]pyrazin-6-yl)(imino)methyl)hydrazine-1-carboxylate (BOC-Amidrazone)

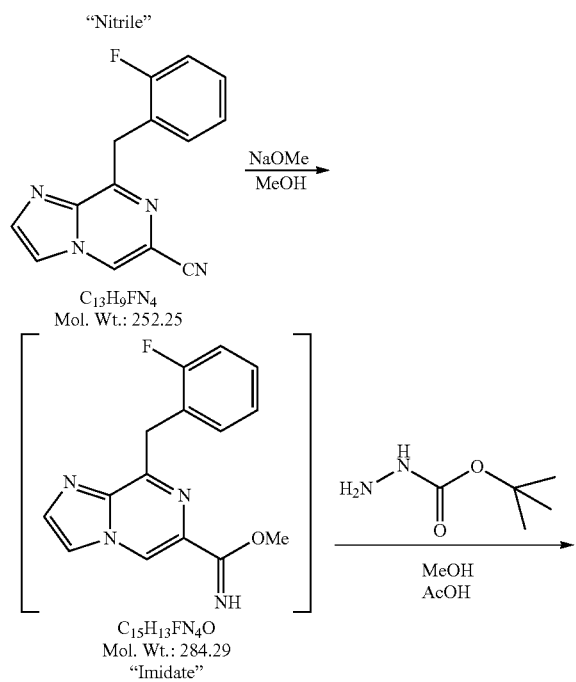

Charged 1 mol (252.25 g) of the Nitrile compound to a 2 L cylindrical reactor equipped with a mechanical stirrer, followed by dry methanol (1.5 L). Stirred at 120-140 RPM to give an ochre, grainy suspension. To the suspension, 5 mol % (100 mL 0.5M soln.) sodium methoxide in methanol was added at room temperature. The reactor jacket temperature was set to 18° C. and the mixture was stirred under nitrogen until HPLC indicated complete conversion to the intermediate methyl imidate (LC-MS: 100 A % MH$^+$ 285). 1.03 eq (136 g) t-butyl carbazate was then added in portions over 15 min. The temperature dropped to 9.2° C. and acetic acid (0.1 eq., 5.7 mL) was added slowly via syringe through septum. The temperature of the reaction mixture slowly rose from 11.2° C. to 17.2° C., resulting in a clear, coffee-brown solution. The reactor jacket temperature was raised to 18° C. and the stirring rate was increased to 165 RPM. After 1 h, a very thick yellow suspension was formed (temperature of the reaction mixture at~21° C.). Additional dry MeOH (550 mL) was then added. After ~24 h, LC-MS indicated complete conversion to the BOC-Amidrazone (MH$^+$ 385) with no methyl imidate detectable by LC-MS. The suspension was cooled to 8-10° C. and 0.06 eq. (60 mL) 1M aq. NaOH was added, followed by sat. aq. NaCl (150 mL) and DI water (200 mL). The resulting mixture was stirred for several hours, before adjusting the pH to 8-9 with 10% aq. Sodium carbonate. The resulting mixture was then diluted with water (250 mL) and filtered over a 2 L medium poros. glass frit, washed with DI water (3×300 mL), and suction dried on the filter for ~45 min. The wetcake was washed with n-heptane (4×200 mL) and suction-dried on the filter for 1 h, then dried to constant weight in the vacuum drying oven at 40° C. The product was obtained as a light yellow, powdery material 358.86 g (93%). Mp (DSC) 181° C. HPLC (RP) [240 nm]: 99.8 A %. MS: MH+385 (100%).

$^1$H-NMR (D$_6$-DMSO): δ ppm 1.47 (s, 9H), 4.56 (s, 2H), 6.34 (s, 2H), 7.12 (t, J=7.48 Hz, 1H), 7.15-7.21 (m, 1H), 7.25-7.33 (m, 1H), 7.42 (t, J=7.63 Hz, 1H), 7.82 (s, 1H), 8.29 (s, 1H), 9.00-9.09 (m, 1H), 9.13 (br s, 1H).

$^{13}$C-NMR (D$_6$-DMSO): δ ppm 28.15, 31.91, 78.44, 115.04, 116.28, 116.50, 124.14, 124.37, 128.56, 131.58, 131.79, 135.40, 139.09, 142.53, 149.66, 152.87, 160.39.

Synthesis of 8-(2-fluorobenzyl)-6-(3-(trifluoromethyl)-1H-1,2,4-triazol-5-yl)imidazo[1,2-a]pyrazine (Compound IF)

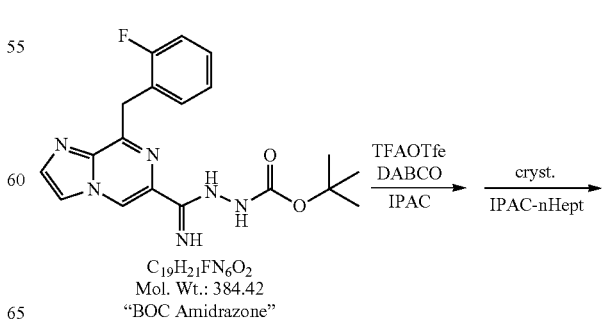

37

-continued

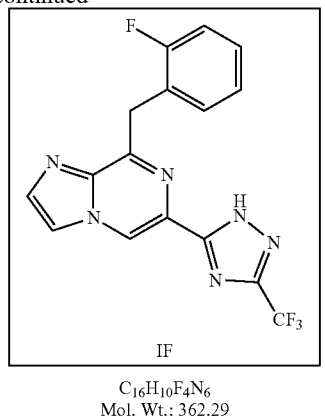

C$_{16}$H$_{10}$F$_4$N$_6$
Mol. Wt.: 362.29

Charged 50 mmol (19.22 g) of the BOC-Amidrazone and 2.2 eq. DABCO (12.34 g) into a 500 ml pear shape flask with a magnetic stir bar. Isopropyl acetate (300 mL) was then added and the mixture was stirred under nitrogen for 2 min at room temp, resulting in a white, thin suspension. To the suspension 2,2,2-trifluoroethyl trifluoroacetate (TFAOTfe or CF$_3$C(=O)OCH$_2$CF$_3$, 2.5 eq., 25 g) was added, and the suspension was stirred at room temp. under nitrogen until HPLC & LC-MS showed complete conversion of the starting material. The resulting suspension was washed sequentially with saturated aqueous sodium bicarbonate, saturated aqeuous sodium chloride and distilled water. The organic phase was filtered over a short silica gel/celite plug and concentrated to a small volume (~50-70 mL) at the rotavap. (waterbath temp.: 45-50° C.). The warm suspension was immediately diluted with n-heptane (150 mL), stirred for 2 hours while slowly cooling to 20°, and then stirred for another 2 hours to 5°, and filtered. The wet cake was washed with n-heptane (2×50 mL) and dried in the vacuum drying oven to constant weight. The product was obtained as snowy white powder 16.7 g (92%). Mp (DSC) 196° C. HPLC (RP) [240 nm]: 99.8 A %. MS: MH+363 (100%).

$^1$H-NMR (D$_6$-DMSO): δ ppm 4.60 (s, 2H) 7.05-7.11 (m, 1H) 7.14-7.20 (m, 1H) 7.22-7.29 (m, 1H) 7.43 (br t, J=7.63 Hz, 1H) 7.84-7.87 (m, 1H) 8.23-8.27 (m, 1H) 9.44 (d, J=1.83 Hz, 1H) 15.43 (br s, 1H).

$^{13}$C-NMR (D$_6$-DMSO): δ ppm 160.90, 158.95, 154.13, 152.73, 152.43, 151.76, 138.89, 135.50, 130.91, 130.87, 128.34, 128.27, 126.39, 124.11, 124.02, 122.47, 120.33, 119.12, 118.18, 116.68, 116.04, 115.01, 114.84, 31.64, 31.61.

$^{19}$F-NMR (D$_6$-DMSO): δ ppm −116.96, −63.93.

All references cited herein are expressly incorporated by reference in their entireties.

The invention claimed is:

1. A process for preparing a compound represented by Formula (IA):

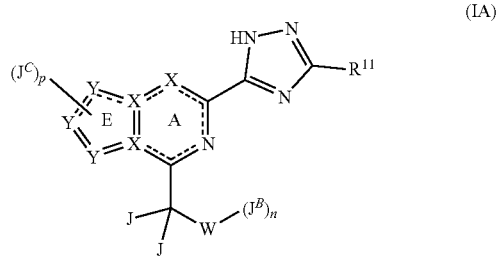

(IA)

38 wherein:

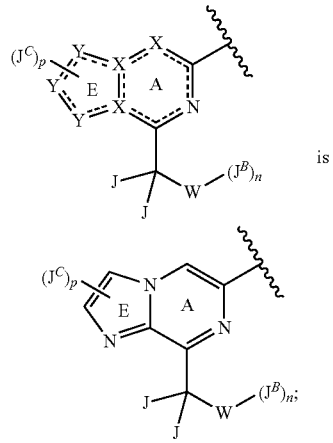

is (i) W is ring B;
ring B is phenyl or a 5- or 6-membered heteroaryl, wherein the 5- or 6-membered heteroaryl contains 1 or 2 N ring heteroatoms;
each J is independently H or CH$_3$;
each J$^B$ is independently halo, CN, C$_{1-6}$ aliphatic, OR$^B$, or a C$_{3-8}$ cycloaliphatic ring, wherein each C$_{1-6}$ aliphatic and C$_{3-8}$ cycloaliphatic ring is optionally and independently substituted with 1, 2, or 3 independently selected R$^3$ substituents;
each R$^B$ is independently C$_{1-6}$ aliphatic or a C$_{3-8}$ cycloaliphatic ring, wherein each C$_{1-6}$ aliphatic and C$_{3-8}$ cycloaliphatic ring is optionally and independently substituted with 1, 2, or 3 independently selected R$^{3a}$ substituents; and
each R$^{3a}$ is independently halo, CN, C$_{1-4}$ alkyl, C$_{1-4}$ haloalkyl, OC$_{1-4}$ alkyl, or OC$_{1-4}$ haloalkyl; or
(ii) W is ring B;
ring B is C$_{3-7}$ cycloalkyl;
each J is independently H;
each J$^B$ is independently halo, CN, C$_{1-6}$ aliphatic, or OR$^{B1}$, wherein each C$_{1-6}$ aliphatic is optionally and independently substituted with 1, 2, or 3 independently selected R$^3$ substituents;
each R$^{B1}$ is independently H, C$_{1-6}$ aliphatic, or a C$_{3-8}$ cycloaliphatic ring, wherein each C$_{1-6}$ aliphatic and C$_{3-8}$ cycloaliphatic ring is optionally and independently substituted with 1, 2, or 3 independently selected R$^{3b}$ substituents; and
each R$^{3b}$ is independently halo, CN, C$_{1-4}$ alkyl, C$_{1-4}$ haloalkyl, OC$_{1-4}$ alkyl, or OC$_{1-4}$ haloalkyl;
each J$^C$ is independently H, halo, CN, C$_{1-4}$ aliphatic, or OC$_{1-4}$ alkyl, wherein each C$_{1-4}$ aliphatic and OC$_{1-4}$ alkyl is optionally and independently substituted with 1, 2, or 3 substituents independently selected form the group consisting of halo, OH, OC$_{1-4}$ alkyl, and OC$_{1-4}$ haloalkyl;
each R$^3$ is independently halo, CN, C$_{1-4}$ alkyl, C$_{1-4}$ haloalkyl, OC$_{1-4}$ alkyl, or OC$_{1-4}$ haloalkyl;
R$^{11}$ is C$_{1-6}$ alkyl, C$_{2-6}$ alkenyl, or C$_{2-6}$ alkynyl, wherein the C$_{1-6}$ alkyl is optionally substituted with 1, 2, or 3 independently selected R$^{15}$ substituents, and further wherein the C$_{2-6}$ alkenyl or C$_{2-6}$ alkynyl is optionally substituted with 1 or 2 independently selected R$^{b2}$ substituents;

each $R^{15}$ is independently halo, $C(O)R^{b2}$, $C(O)NR^{a2}R^{b2}$, $NR^{a2}R^{b2}$, $C(O)OR^{b2}$, $OR^{b2}$, $OC_{2\text{-}4}$ alkenyl, $OC(O)NR^{a2}R^{b2}$, $SR^{b2}$, $C_{3\text{-}4}$ cycloalkyl, 3- to 10-membered heterocyclyl, phenyl, or a 5- or 6-membered heteroaryl, wherein each 3- to 10-membered heterocyclyl and 5- or 6-membered heteroaryl independently contains 1, 2, or 3 ring heteroatoms independently selected from the group consisting of N, O, and S, and further wherein each $C_{3\text{-}4}$ cycloalkyl, 3- to 10-membered heterocyclyl, phenyl, and 5- or 6-membered heteroaryl is optionally and independently substituted with 1, 2, or 3 independently selected $R^{18}$ substituents;

each $R^{18}$ is independently halo, $C_{1\text{-}6}$ alkyl, $C_{1\text{-}6}$ haloalkyl, OH, $OC_{1\text{-}6}$ alkyl, or phenyl;

each $R^{a2}$ is independently H, $C_{1\text{-}6}$ alkyl, $C_{1\text{-}6}$ haloalkyl, or $C(O)R^{b2}$;

each $R^{b2}$ is independently H, $C_{1\text{-}6}$ alkyl, or $C_{1\text{-}6}$ haloalkyl;

n is 0, 1, 2, or 3; and p is 1 or 2;

wherein the process comprises the following step:

reacting a compound represented by Formula (IIA):

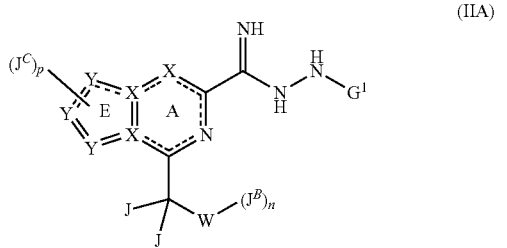

or a salt thereof, wherein:

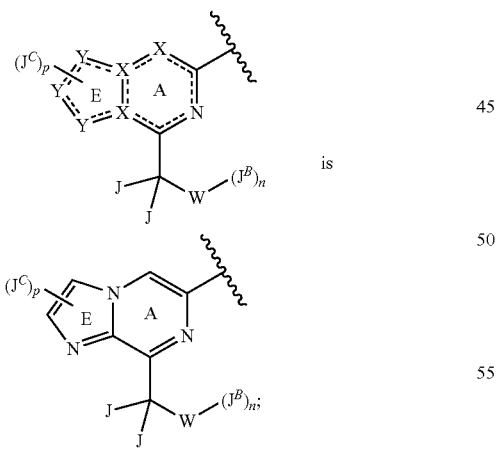

(i) W is ring B;

ring B is phenyl or a 5- or 6-membered heteroaryl, wherein the 5- or 6-membered heteroaryl contains 1 or 2 N ring heteroatoms;

each J is independently H or $CH_3$;

each $J^B$ is independently halo, CN, $C_{1\text{-}6}$ aliphatic, $OR^B$, or a $C_{3\text{-}8}$ cycloaliphatic ring, wherein each $C_{1\text{-}6}$ aliphatic and $C_{3\text{-}8}$ cycloaliphatic ring is optionally and independently substituted with 1, 2, or 3 independently selected $R^3$ substituents;

each $R^B$ is independently $C_{1\text{-}6}$ aliphatic or a $C_{3\text{-}8}$ cycloaliphatic ring, wherein each $C_{1\text{-}6}$ aliphatic and $C_{3\text{-}8}$ cycloaliphatic ring is optionally and independently substituted with 1, 2, or 3 independently selected $R^{3a}$ substituents; and each $R^{3a}$ is independently halo, CN, $C_{1\text{-}4}$ alkyl, $C_{1\text{-}4}$ haloalkyl, $OC_{1\text{-}4}$ alkyl, or $OC_{1\text{-}4}$ haloalkyl; or (ii) W is ring B;

ring B is $C_{3\text{-}7}$ cycloalkyl;

each J is independently H;

each $J^B$ is independently halo, CN, $C_{1\text{-}6}$ aliphatic, or $OR^{B1}$, wherein each $C_{1\text{-}6}$ aliphatic is optionally and independently substituted with 1, 2, or 3 independently selected $R^3$ substituents;

each $R^{B1}$ is independently H, $C_{1\text{-}6}$ aliphatic, or a $C_{3\text{-}8}$ cycloaliphatic ring, wherein each $C_{1\text{-}6}$ aliphatic and $C_{3\text{-}8}$ cycloaliphatic ring is optionally and independently substituted with 1, 2, or 3 independently selected $R^{3b}$ substituents; and each $R^{3b}$ is independently halo, CN, $C_{1\text{-}4}$ alkyl, $C_{1\text{-}4}$ haloalkyl, $OC_{1\text{-}4}$ alkyl, or $OC_{1\text{-}4}$ haloalkyl;

each $J^C$ is independently H, halo, CN, $C_{1\text{-}4}$ aliphatic, or $OC_{1\text{-}4}$ alkyl, wherein each $C_{1\text{-}4}$ aliphatic and $OC_{1\text{-}4}$ alkyl is optionally and independently substituted with 1, 2, or 3 substituents independently selected form the group consisting of halo, OH, $OC_{1\text{-}4}$ alkyl, and $OC_{1\text{-}4}$ haloalkyl;

each $R^3$ is independently halo, CN, $C_{1\text{-}4}$ alkyl, $C_{1\text{-}4}$ haloalkyl, $OC_{1\text{-}4}$ alkyl, or $OC_{1\text{-}4}$ haloalkyl;

$G^1$ is $CH_2OCH_2CH_2Si(CH_3)_3$, $CH_2CH_2Si(CH_3)_3$, $CH_2CH(Ph)Si(CH_3)_3$, $C(O)CH_3$, $C(O)CF_3$, $C(O)CH_2$-phenyl, $C(O)OCH_2CCl_3$, $C(O)OCH_2$-phenyl, $C(O)OCH_2$-(9-fluorenyl), $C(O)OCH_2CH_2Si(CH_3)_3$, $C(O)OCH_2CH=CH_2$, $C(O)OC(CH_3)_3$, $OSi[CH(CH_3)_2]_3$, $S(O)_2CH_3$, $S(O)_2$-(4-bromophenyl), $S(O)_2$-(4-methylphenyl), $S(O)_2$-(2-nitrophenyl), or $S(O)_2$-(4-nitrophenyl);

n is 0, 1, 2, or 3; and p is 1 or 2;

with a compound of the following formula:

$R^{11}C(O)OE'$, wherein:

E' is $C_{1\text{-}6}$ alkyl, $C_{1\text{-}6}$ haloalkyl, heterocyclyl, phenyl, or heteroaryl, wherein the heterocyclyl, phenyl, or heteroaryl is optionally substituted with 1, 2, 3, 4, 5, or 6 substituents independently selected from the group consisting of halo, CN, $NO_2$, =O, $S(O)_2OH$, and $S(O)_2OC_{1\text{-}6}$ alkyl; and $R^{11}$ is $C_{1\text{-}6}$ alkyl, $C_{2\text{-}6}$ alkenyl, or $C_{2\text{-}6}$ alkynyl, wherein the $C_{1\text{-}6}$ alkyl is optionally substituted with 1, 2, or 3 independently selected $R^{15}$ substituents, and further wherein the $C_{2\text{-}6}$ alkenyl or $C_{2\text{-}6}$ alkynyl is optionally substituted with 1 or 2 independently selected $R^{b2}$ substituents;

each $R^{15}$ is independently halo, $C(O)R^{b2}$, $C(O)NR^{a2}R^{b2}$, $NR^{a2}R^{b2}$, $NR^{b2}C(O)OR^{b2}$, $OR^{b2}$, $OC_{2\text{-}4}$ alkenyl, $OC(O)NR^{a2}R^{b2}$, $SR^{b2}$, $C_{3\text{-}4}$ cycloalkyl, 3- to 10-membered heterocyclyl, phenyl, or a 5- or 6-membered heteroaryl, wherein each 3- to 10-membered heterocyclyl and 5- or 6-membered heteroaryl independently contains 1, 2, or 3 ring heteroatoms independently selected from the group consisting of N, O, and S, and further wherein each $C_{3\text{-}4}$ cycloalkyl, 3- to 10-membered heterocyclyl, phenyl, and 5- or 6-membered heteroaryl is optionally and independently substituted with 1, 2, or 3 independently selected $R^{18}$ substituents;

each $R^{18}$ is independently halo, $C_{1-6}$ alkyl, $C_{1-6}$ haloalkyl, OH, $OC_{1-6}$ alkyl, or phenyl;

each $R^{a2}$ is independently H, $C_{1-6}$ alkyl, $C_{1-6}$ haloalkyl, or $C(O)R^{b2}$; and each $R^{b2}$ is independently H, $C_{1-6}$ alkyl, or $C_{1-6}$ haloalkyl;

in the presence of a base selected from the group consisting of LiOH, NaOH, KOH, $NaOCH_3$, $N(alkyl)_3$, 1,8-diazabicyclo(5.4.0)undec-7-ene (DBU), 1,5-diazabicyclo[4.3.0]non-5-ene (DBN), guanidine, 1,1,3,3-tetramethylguanidine, 4-dimethylaminopyridine (DMAP), and 1,4-diazabicyclo[2.2.2]octane (DABCO).

2. The process of claim 1, wherein $G^1$ is $C(O)CH_3$, $C(O)CF_3$, $C(O)CH_2$-phenyl, $C(O)OCH_2CCl_3$, $C(O)OCH_2$-phenyl, $C(O)OCH_2$-(9-fluorenyl), $C(O)OCH_2CH=CH_2$, $C(O)OC(CH_3)_3$, $S(O)_2CH_3$, $S(O)_2$-(4-bromophenyl), $S(O)_2$-(4-methylphenyl), $S(O)_2$-(2-nitrophenyl), or $S(O)_2$-(4-nitrophenyl).

3. The process of claim 2, wherein $G^1$ is $C(O)CH_3$, $C(O)CF_3$, $C(O)CH_2$-phenyl, $C(O)OCH_2CCl_3$, $C(O)OCH_2$-phenyl, $C(O)OCH_2$-(9-fluorenyl), $C(O)OC(CH_3)_3$, $S(O)_2CH_3$, $S(O)_2$-(4-bromophenyl), $S(O)_2$-(4-methylphenyl), $S(O)_2$-(2-nitrophenyl), or $S(O)_2$-(4-nitrophenyl).

4. The process of claim 1, wherein E' is $C_{1-6}$ alkyl, $C_{1-6}$ haloalkyl, heterocyclyl, phenyl, or heteroaryl, wherein the heterocyclyl, phenyl, or heteroaryl is optionally substituted with 1, 2, or 3 substituents independently selected from the group consisting of halo, CN, $NO_2$, =O, $S(O)_2OH$, and $S(O)_2OC_{1-6}$ alkyl.

5. The process of claim 1, wherein $R^{11}$ is $C_{1-6}$ alkyl, wherein the $C_{1-6}$ alkyl is optionally substituted with 1, 2, or 3 independently selected halo substituents.

6. The process of claim 1, wherein the base is selected from the group consisting of $N(alkyl)_3$, 1,8-diazabicyclo(5.4.0)undec-7-ene (DBU), 1,5-diazabicyclo[4.3.0]non-5-ene (DBN), guanidine, 1,1,3,3-tetramethylguanidine, 4-dimethylaminopyridine (DMAP), and 1,4-diazabicyclo[2.2.2]octane (DABCO).

7. The process of claim 1, wherein:
the compound represented by Formula (IA) is represented by Formula (ID):

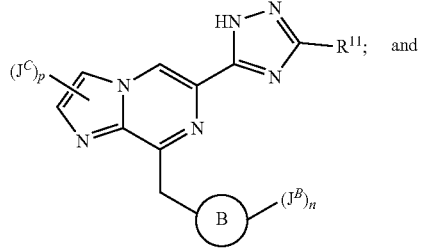

(ID)

the compound represented by Formula (IIA) is represented by Formula (IID):

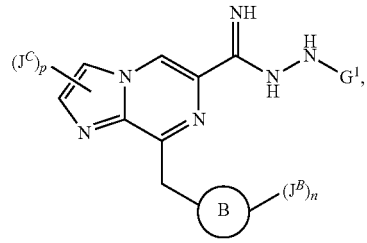

(IID)

or a salt thereof.

8. The process of claim 7, wherein:
the compound represented by Formula (ID) is represented by Formula (IE):

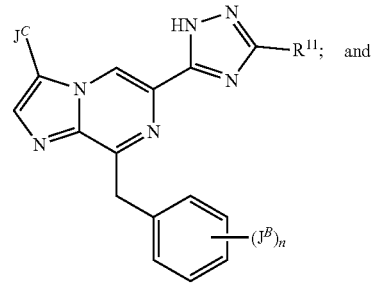

(IE)

the compound represented by Formula (IID) is represented by Formula (IIE):

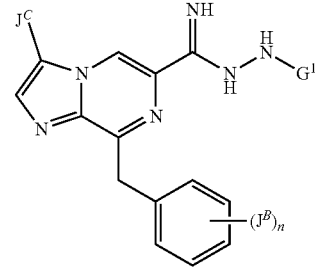

(IIE)

or a salt thereof.

9. The process of claim 8, wherein:
the compound represented by Formula (IE) is represented by Formula (IF):

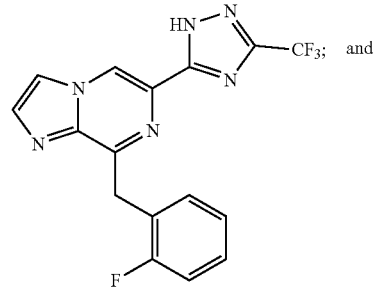

(IF)

the compound represented by Formula (IIE) is represented by Formula (IIF):

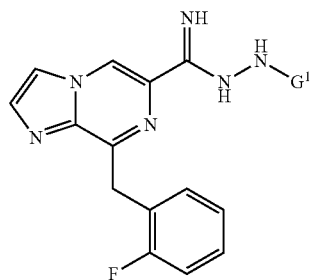
(IIF)

or a salt thereof.

10. The process of claim 1, wherein the compound of Formula (IA) is represented by Formula (IF):

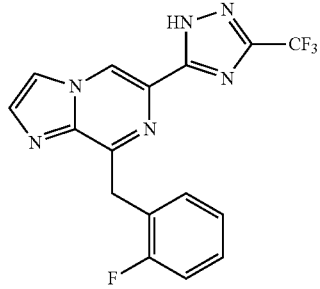
(IF)

wherein the process comprises the following step:
reacting a compound represented by Formula (IIFa):

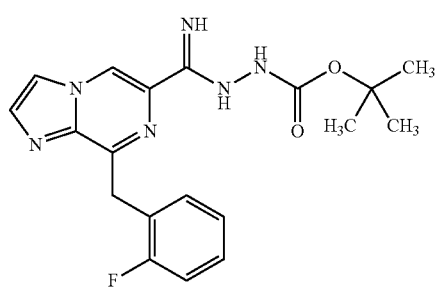
(IIFa)

or a salt thereof;
with a compound of the following formula:

$R^{11}C(O)OE'$, wherein:
E' is $CH_2CF_3$; and
$R^{11}$ is $CF_3$;
in the presence of a base selected from the group consisting of N(alkyl)$_3$, 1,8-diazabicyclo(5.4.0)undec-7-ene (DBU), 1,5-diazabicyclo[4.3.0]non-5-ene (DBN), guanidine, 1,1,3,3-tetramethylguanidine, 4-dimethylaminopyridine (DMAP), and 1,4-diazabicyclo[2.2.2]octane (DABCO).

11. The process of claim 10, wherein the base is 1,4-diazabicyclo[2.2.2]octane (DABCO).

* * * * *